US011235040B2

(12) United States Patent
Lindstrom et al.

(10) Patent No.: US 11,235,040 B2
(45) Date of Patent: Feb. 1, 2022

(54) ACETYLCHOLINE RECEPTOR-SPECIFIC IMMUNOSUPPRESSIVE COMPOSITIONS AND METHODS OF TREATMENT OF MYASTHENIA GRAVIS

(71) Applicant: THE TRUSTEES OF THE UNIVERSITY OF PENNSYLVANIA, Philadelphia, PA (US)

(72) Inventors: Jon Lindstrom, Radnor, PA (US); Jie Luo, Dresher, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 675 days.

(21) Appl. No.: 15/511,363

(22) PCT Filed: Sep. 14, 2015

(86) PCT No.: PCT/US2015/049924
§ 371 (c)(1),
(2) Date: Mar. 15, 2017

(87) PCT Pub. No.: WO2016/044137
PCT Pub. Date: Mar. 24, 2016

(65) Prior Publication Data
US 2019/0160159 A1 May 30, 2019

Related U.S. Application Data

(60) Provisional application No. 62/050,405, filed on Sep. 15, 2014.

(51) Int. Cl.
*A61K 38/17* (2006.01)
*C07K 14/705* (2006.01)
*C07K 19/00* (2006.01)
*A61K 39/00* (2006.01)
*A61P 21/04* (2006.01)

(52) U.S. Cl.
CPC .......... *A61K 39/0008* (2013.01); *A61P 21/04* (2018.01); *A61K 2039/545* (2013.01); *A61K 2039/55505* (2013.01); *A61K 2039/55566* (2013.01); *A61K 2039/57* (2013.01)

(58) Field of Classification Search
None
See application file for complete search history.

(56) References Cited

U.S. PATENT DOCUMENTS

| 9,181,344 B2 | 11/2015 | Losen et al. |
| 2011/0237688 A1 | 9/2011 | Christadoss et al. |
| 2012/0076808 A1 | 3/2012 | Wang et al. |
| 2014/0161831 A1 | 6/2014 | Blalock et al. |

FOREIGN PATENT DOCUMENTS

EP  1806582  5/2011

OTHER PUBLICATIONS

Lindstrom et al., Myasthenia Gravis and the Tops and Bottoms of AChRs Antigenic Structure of the MIR and Specific Immunosuppression of EAMG Using AChR Cytoplasmic Domains, 2008, Ann N Y Acad Sci. 2008 ; 1132: 29-41 (Year: 2008).*
Fuichs et al., Experimental Autoimmune Myasthenia Gravis (EAMG): From immunochemical characterization to therapeutic approaches, 2014, Journal of Autoimmunity 54:51-59 (Year: 2014).*
International Patent Application No. PCT/US2015/049924, Notification of Transmittal of the International Search Report and the Written Opinion of the International Searching Authority, or the Declaration, dated Jan. 8, 2017, 14 pages.
Luo et al. "Specific Immunotherapy of Experimental Myasthenia Gravis by a Novel Mechanism," Ann Neurol. Apr. 2010, vol. 67(4), 441-451.
Tagliabue et al. "Vaccine Adjuvants: The Dream becomes Real," Hum Vaccines, Sep. 2008, 4(5), 347-349.
Marrack et al. "Towards an understanding of teh adjuvant action of aluminium," Nat. Rev. Immunol., Apr. 2009, 9(4), 287-293.
Luo et al. "AChR-specific immunosuppressive therapy of myasthenia gravis," Biochemical Pharmacology, Jul. 2015, 37, 609-619.
Lindstrom; "Neuronal Nicotinic Acetylcholine Receptors"; Ion Channels, vol. 4, edited by Toshio Narahashi; Plenum Press, New York, 1996; 38 pages.
Abbas A. K., K. M. Murphy, A. Sher; 1996; Functional diversity of helper T lymphocytes; Nature 383: 787-793.
Im, Sin-Hyeong, et al.; 2000; Role of tolerogen conformation in induction of oral tolerance in experimental autoimmune myasthenia gravis; J. Immunol. 165: 3599-3605.
Berrih-Aknin S., R. Le Panse; 2014; Myasthenia gravis: a comprehensive review of immune dysregulation and etiological mechanisms; J. Autoimmun 52: 90-100.
Brine D., G. A. Denomme, A. H. Lazarus; 2009; Mechanisms of anti-D action in the prevention of hemolytic disease of the fetus and newborn: what can we learn from rodent models?; Curr. Opin. Hematol. 16:488-496.
Conti-Fine B. M., M. Milani, H. J. Kaminski; 2006. Myasthenia gravis: past, present, and future; J. Clin. Invest. 116: 2843-2854.

(Continued)

*Primary Examiner* — Joanne Hama
*Assistant Examiner* — Jon M Lockard
(74) *Attorney, Agent, or Firm* — Morgan, Lewis & Bockius LLP

(57) ABSTRACT

In one embodiment a vaccine composition comprises two or three AChR subunit constructs and an adjuvant. In some embodiments the AChR subunit construct is an AChR α1 subunit construct, an AChR β1 subunit construct, an AChR γ subunit construct, an AChR δ subunit construct, or an AChR ε subunit construct. In another embodiment, the invention provides a method of treating myasthenia gravis in a patient in need thereof, comprising administering a vaccine composition comprising one or more acetylcholine receptor subunit constructs selected from the group consisting of AChR α1 subunit, AChR β1 subunit, AChR γ subunit, AChR δ subunit, AChR ε subunit, a fragment thereof, and a combination thereof, and an adjuvant.

16 Claims, 21 Drawing Sheets
Specification includes a Sequence Listing.

(56) References Cited

OTHER PUBLICATIONS

Cousens L. P., Y. Su, E. McClaine, X. Li, F. Terry, R. Smith, J. Lee, W. Martin, D. W. Scott, A. S. De Groot; 2013; Application of IgG-derived natural Treg epitopes (IgG Tregitopes) to antigen-specific tolerance induction in a murine model of type 1 diabetes; J. Diabetes Res. 2013: 621693.

Cribbs D. H., A. Ghochikyan, V. Vasilevko, M. Tran, I. Petrushina, N. Sadzikava, D. Babikyan, P. Kesslak, T. Kieber-Emmons, C. W. Cotman, M. G. Agadjanyan; 2003; Adjuvant-dependent modulation of Th1 and Th2 responses to Immunization with β-amyloid.;Int. Immunol. 15: 505-514.

Dalakas M. C.; 2013; Novel future therapeutic options in myasthenia gravis; Autoimmun. Rev. 12: 936-941.

Dixon F. J., H. Jacot-Guillarmod, P. J. McConahey; 1967; The effect of passively administered antibody on antibody synthesis; J. Exp. Med. 125: 1119-1135.

Drachman D. B., R. N. Adams, R. Hu, R. J. Jones, R. A. Brodsky; 2008; Rebooting the immune system with high-dose cyclophosphamide for treatment of refractory myasthenia gravis; Ann. N. Y. Acad. Sci. 1132: 305-314.

Faria A. M., H. L. Weiner; 2006; Oral tolerance: therapeutic implications for autoimmune diseases; Clin. Dev. Immunol. 13: 143-157.

Gold R., M. C. Dalakas, K. V. Toyka; 2003; Immunotherapy in autoimmune neuromuscular disorders; Lancet Neurol. 2:22-32.

Gomez A. M., K. Vrolix, P. Martinez-Martinez, P. C. Molenaar, M. Phemambucq, E. van der Esch, H. Duimel, F. Verheyen, R. E. Voll, R. A. Manz, et al.; 2011; Proteasome inhibition with bortezomib depletes plasma cells and autoantibodies in experimental autoimmune myasthenia gravis; J. Immunol. 186: 2503-2513.

Gomez A. M., N. Willcox, P. C. Molenaar, W. Buurman, P. Martinez-Martinez, M. H. De Baets, M. Losen; 2012; Targeting plasma cells with proteasome inhibitors: possible roles in treating myasthenia gravis?; Ann. N. Y. Acad. Sci. 1274: 48-59.

Heyman B.; 2000; Regulation of antibody responses via antibodies, complement, and Fc receptors; Annu. Rev. Immunol. 18: 709-737.

Hughes E. G., X. Peng, A. J. Gleichman, M. Lai, L. Zhou, R. Tsou, T. D. Parsons, D. R. Lynch, J. Dalmau, R. J. Balice-Gordon; 2010; Cellular and synaptic mechanisms of anti-NMDA receptor encephalitis; J. Neurosci. 30: 5866-5875.

Jang E., W. S. Cho, M. L. Cho, H. J. Park, H. J. Oh, S. M. Kang, D. J. Paik, J. Youn; 2011; Foxp3+ regulatory T cells control humoral autoimmunity by suppressing the development of long-lived plasma cells; J. Immunol. 186: 1546-1553.

Keesey J. C.; 2004; Clinical evaluation and management of myasthenia gravis; Muscle Nerve 29: 484-505.

Lennon V. A., J. M. Lindstrom, M. E. Seybold; 1975; Experimental autoimmune myasthenia: A model of myasthenia gravis in rats and guinea pigs; J. Exp. Med. 141: 1365-1375.

Lennon V. A., J. M. Lindstrom, M. E. Seybold; 1976; Experimental autoimmune myasthenia gravis: cellular and humoral immune responses; Ann. N. Y. Acad. Sci. 274: 283-299.

Lennon V. A., E. H. Lambert, K. R. Leiby, T. B. Okarma, S. Talib; 1991; Recombinant human acetylcholine receptor α-subunit induces chronic experimental autoimmune myasthenia gravis; J. Immunol. 146: 2245-2248.

Lindstrom J. M., V. A. Lennon, M. E. Seybold, S. Whittingham; 1976; Experimental autoimmune myasthenia gravis and myasthenia gravis: biochemical and immunochemical aspects; Ann N. Y. Acad. Sci. 274: 254-274.

Lindstrom J. M., B. L. Einarson, V. A. Lennon, M. E. Seybold; 1976; Pathological mechanisms in experimental autoimmune myasthenia gravis. I. Immunogenicity of syngeneic muscle acetylcholine receptor and quantitative extraction of receptor and antibody-receptor complexes from muscles of rats with experimental autoimmune myasthenia gravis; J. Exp. Med. 144: 726-738.

Lindstrom J. M., M. E. Seybold, V. A. Lennon, S. Whittingham, D. D. Duane; 1976; Antibody to acetylcholine receptor in myasthenia gravis. Prevalence, clinical correlates, and diagnostic value. Neurology 26: 1054-1059.

Yi H. J., C. S. Chae, J. S. So, S. J. Tzartos, M. C. Souroujon, S. Fuchs, S. H. Im; 2008; Suppression of experimental myasthenia gravis by a B-cell epitope-free recombinant acetylcholine receptor; Mol. Immunol. 46: 192-201.

Lindstrom J. M.; 2000; Acetylcholine receptors and myasthenia; Muscle Nerve 23: 453-477.

Luo et al.; 2014; Antigen-Specific Immunotherapeutic Vacine for Experimental Autoimmune Myasthenia Gravis; J. Immunol. 193: 5044-5055.

Loutrari H., A. Kokla, S. J. Tzartos. 1992. Passive transfer of experimental myasthenia gravis via antigenic modulation of acetylcholine receptor. Eur. J. Immunol. 22: 2449-2452.

Luo J., P. Taylor, M. Losen, M. H. de Baets, G. D. Shelton, J. Lindstrom; 2009; Main immunogenic region structure promotes binding of conformation-dependent myasthenia gravis autoantibodies, nicotinic acetylcholine receptor conformation maturation, and agonist sensitivity; J. Neurosci. 29: 13898-13908.

Luo J., A. Kuryatov, J. M. Lindstrom; 2010; Specific immunotherapy of experimental myasthenia gravis by a novel mechanism; Ann Neurol. 67: 441-451.

Luo J., J. Lindstrom; 2012. Myasthenogenicity of the main immunogenic region and endogenous muscle nicotinic acetylcholine receptors; Autoimmunity 45: 245-252.

Luo J., Lindsrtom, J.; 2015; AChR-Specific Immunosuppressive Therapy of Myasthenia Gravis. Biochemical Pharmacology; https://doi.org/10.1016/j.bcp.2015.07.011.

Maiti P. K., T. Feferman, S. H. Im, M. C. Souroujon, S. Fuchs; 2004; Immunosuppression of rat myasthenia gravis by oral administration of a syngeneic acetylcholine receptor fragment; J. Neuroimmunol. 152: 112-120.

Mamalaki A., N. Trakas, S. J. Tzartos; 1993; Bacterial expression of a single-chain Fv fragment which efficiently protects the acetylcholine receptor against antigenic modulation caused by myasthenic antibodies; Eur. J. Immunol. 23: 1839-1845.

Marrack P., A. S. McKee, M. W. Munks; 2009; Towards an understanding of the adjuvant action of aluminium; Nat. Rev. Immunol. 9: 287-293.

McGuirk P., K. H. Mills; 2002; Pathogen-specific regulatory T cells provoke a shift in the Th1/Th2 paradigm in immunity to infectious diseases; Trends Immunol. 23: 450-455.

Medgyesi G. A., K. Miklós, J. Kulics, G. Füst, J. Gergely, H. Bazin; 1981; Classes and subclasses of rat antibodies: reaction with the antigen and interaction of the complex with the complement system; Immunology 43: 171-176.

Na D., D. Kim, D. Lee; 2006; Mathematical modeling of humoral immune response suppression by passively administered antibodies in mice; J. Theor. Biol. 241: 830-851.

Phillips L. H.; 2004; The epidemiology of myasthenia gravis; Semin. Neurol 24: 17-20.

Rødgaard A., F. C. Nielsen, R. Djurup, F. Somnier, S. Gammeltoft; 1987; Acetylcholine receptor antibody in myasthenia gravis: predominance of IgG subclasses 1 and 3; Clin. Exp. Immunol. 67: 82-88.

Sanders D. B., T. M. Burns, G. R. Cutter, J. M. Massey, V. C. Juel, L. Hobson-Webb; Muscle Study Group; 2014; Does change in acetylcholine receptor antibody level correlate with clinical change in myasthenia gravis?; Muscle Nerve 49: 483-486.

Sine S. M.; 2012; End-plate acetylcholine receptor: structure, mechanism, pharmacology, and disease; Physiol. Rev. 92: 1189-1234.

Steinman L., J. T. Merrill, I. B. McInnes, M. Peakman; 2012; Optimization of current and future therapy for autoimmune diseases; Nat. Med. 18: 59-65.

Tüzün E., R. Huda, P. Christadoss; 2011; Complement and cytokine based therapeutic strategies in myasthenia gravis. J. Autoimmun; 37: 136-143.

Tzartos S. J., M. E. Seybold, J. M. Lindstrom; 1982; Specificities of antibodies to acetylcholine receptors in sera from myasthenia gravis patients measured by monoclonal antibodies; Proc. Natl. Acad Sci. USA 79: 188-192.

(56) References Cited

OTHER PUBLICATIONS

Wekerle H., R. Hohlfeld; 2010; Zero tolerance (to acetylcholine receptor) and ways to overcome it; Ann. Neurol. 67: 422-424.

Xiang Z., A. J. Cutler, R. J. Brownlie, K. Fairfax, K. E. Lawlor, E. Severinson, E. U. Walker, R. A. Manz, D. M. Tarlinton, K. G. Smith. 2007. FcγRllb controls bone marrow plasma cell persistence and apoptosis. Nat. Immunol. 8: 419-429.

Xiao B. G., H. Link; 1997; Mucosal tolerance: a two-edged sword to prevent and treat autoimmune diseases; Clin. Immunol. Immunopathol. 85: 119-128.

Blount, et al.; "Characterization of an Adult Muscle Acetylcholine Receptor Subunit by Expression in Fibroblasts"; The Journal of Biological Chemistry, vol. 266, No. 22, Issue of August 5, pp. 14692-14969, 1991; 5 pages.

Herlitze et al.; "Structural determinants of channel conductance in fetal and adult rat muscle acetylcholine receptors" Journal of Physiology, 1996, 493.3, pp. 775-787; 13 pages.

Missias et al.; "Maturation of the Acetylcholine Receptor in Skeletal Muscle: Regulation of the AChR g-to-e Switch"; Developmental Biology 179, 223-238 (1996), Article No. 0253; 16 pages.

Tsunoyama et al.; "Evolution of Nicotinic Acetylcholine Receptor Subunits"; 10 pages.

\* cited by examiner

FIG. 8

ACETYLCHOLINE RECEPTOR-SPECIFIC IMMUNOSUPPRESSIVE COMPOSITIONS AND METHODS OF TREATMENT OF MYASTHENIA GRAVIS

CROSS-REFERENCE TO RELATED APPLICATIONS

This application is a U.S. National Stage Entry of International Patent Application No. PCT/US2015/049924, filed Sep. 14, 2015 entitled, "Acetylcholine Receptor-Specific Immunosuppressive Compositions and Methods of Treatment Of Myasthenia Gravis", which in turn claims the benefit of U.S. Provisional Patent Application No. 62/050,405 filed Sep. 15, 2014 entitled, "Compositions and Methods for Treatment of Myasthenia Gravis," each of which is hereby incorporated by reference in its entirety.

This application claims the benefit of U.S. Provisional Patent Application No. 62/050,405 filed Sep. 15, 2014 entitled, "Compositions and Methods for Treatment of Myasthenia Gravis," which is hereby incorporated by reference in its entirety.

BACKGROUND OF THE INVENTION

Myasthenia gravis (MG) and experimental autoimmune myasthenia gravis (EAMG) are caused by T-cell dependent antibody-mediated autoimmune responses to acetylcholine receptors (AChRs), in which neuromuscular transmission is impaired by loss of AChRs and disruption of postsynaptic membrane morphology. Pathological autoantibodies are directed at extracellular domains of muscle AChRs, especially conformation-dependent epitopes such as the main immunogenic region (MIR). What causes the autoimmune response to AChRs in MG is not known. EAMG can be induced by immunization with AChRs from fish electric organs, mammalian muscle, or by the MIR sequences in a chimera with ACh binding protein that preserves the native conformation of the MIR.

There is currently no cure for MG.

MG is treated with acetylcholinesterase inhibitors (with modest efficacy in improving neurotransmission) and non-specific immunosuppressants (whose beneficial effects may be delayed for months and can cause severe side effects). Although current treatments for MG can help most patients achieve clinical remission, a small but important proportion of MG patients do not tolerate or are resistant to the current treatments. There is no specific immunosuppressive therapy.

BRIEF SUMMARY OF THE INVENTION

In one embodiment the invention provides a vaccine composition comprising one or more acetylcholine receptor subunit constructs. In one embodiment, the acetylcholine receptor subunit is a nicotinic receptor subunit. In yet another embodiment, the subunit is selected from the group consisting of AChR α1 subunit, AChR β1 subunit, AChR γ subunit, AChR δ subunit, AChR ε subunit, and fragments thereof; and an adjuvant. In one embodiment the adjuvant may include an aluminum salt. For example, the adjuvant may include an aluminum salt selected from the group consisting of aluminum hydroxide, aluminum phosphate, aluminum potassium sulfate, and aluminum hydroxyphosphate sulfate.

In another embodiment the adjuvant may be selected from the group consisting of sorbitan trioleate emulsified in squalene oil and polysorbate 80 (e.g. Tween 80), aluminum hydroxide adsorbent, and aluminum hydroxide adsorbent plus monophosphoryl lipid A.

In one embodiment the adjuvant induces a Th2 response. In one embodiment the adjuvant may induce a greater Th2 response than Th1 response. In one embodiment the one or more acetylcholine receptor subunit constructs consists of an AChR β1 subunit construct, an AChR α1 subunit construct, and an AChR γ subunit construct. In another embodiment the one or more acetylcholine receptor subunit constructs consists of an AChR ε subunit construct, an AChR α1 subunit construct, and an AChR γ subunit construct.

In another embodiment, the invention provides a method of treating myasthenia gravis in a patient in need thereof, comprising administering a vaccine composition comprising one or more acetylcholine receptor subunit constructs selected from the group consisting of AChR α1 subunit (SEQ ID NO 1), AChR β1 subunit (SEQ ID NO 2), AChR γ subunit (SEQ ID NO 3), AChR δ subunit (SEQ ID NO 4), AChR ε subunit (SEQ ID NO 5), a fragment thereof, and a combination thereof, and an adjuvant.

In still another embodiment, the invention provides a method of treating or preventing the onset of chronic myasthenia gravis in a patient, comprising administering a vaccine composition comprising one or more acetylcholine receptor subunit constructs selected from the group consisting of an AChR α1 subunit construct, an AChR β1 subunit construct, an AChR γ subunit construct, an AChR δ subunit construct, an AChR ε subunit construct, a fragment thereof, and a combination thereof, and an adjuvant. In one embodiment the patient has acute myasthenia gravis. In another embodiment the patient has chronic myasthenia gravis.

In another embodiment, the invention provides a method of treating acute myasthenia gravis in a patient, comprising administering a vaccine composition comprising one or more acetylcholine receptor subunit constructs selected from the group consisting of an AChR α1 subunit construct, an AChR β1 subunit construct, an AChR γ subunit construct, an AChR δ subunit construct, an AChR ε subunit construct, a fragment thereof, and a combination thereof, and an adjuvant.

In some embodiments of the methods of the invention, the vaccine composition is administered once a week or once every two weeks. In some embodiments of the invention, the vaccine composition administered comprises 1 mg acetylcholine receptor subunit construct, or 0.5 mg acetylcholine receptor subunit construct.

In another embodiment, the invention provides a method of preparing a vaccine composition comprising expressing one or more acetylcholine receptor subunit constructs in bacteria; purifying the one or more acetylcholine receptor subunit constructs; combining the one or more acetylcholine receptor subunit constructs with an adjuvant. In one embodiment the one or more acetylcholine receptor subunit constructs is selected from the group consisting of an AChR α1 subunit construct, an AChR β1 subunit construct, an AChR γ subunit construct, an AChR δ subunit construct, an AChR ε subunit construct, a fragment thereof, and a combination thereof. In one embodiment the adjuvant comprises an aluminum salt. In another embodiment the adjuvant is selected from the group consisting of sorbitan trioleate emulsified in squalene oil and polysorbate 80 (e.g. Tween 80), aluminum hydroxide adsorbent, and aluminum hydroxide adsorbent plus monophosphoryl lipid A.

BRIEF DESCRIPTION OF THE DRAWINGS

The foregoing summary, as well as the following detailed description of embodiments of the compositions and methods for treating myasthenia gravis, will be better understood when read in conjunction with the appended drawings of an exemplary embodiment. It should be understood, however, that the invention is not limited to the precise arrangements and instrumentalities shown.

In the drawings:

FIG. 5. Serum antibodies from previously treated rats were less effective at fixing complement because of isotype switching. These are pooled sera used in FIG. 4G. (A) Sera were mixed with excess MIR/AChBP chimera to allow antibody binding and activation of complement, then complement consumed was assayed. Serum antibodies from the normal rats immunized with Torpedo AChR were effective at fixing complement. In contrast, serum antibodies from the rats previously treated then re-immunized with Torpedo AChR did not fix complement within the tested concentration range, although these sera contained 3-fold more anti-MIR antibodies than did sera from the normal rats immunized with *Torpedo* AChR. (B) MIR/AChBP chimera was used as antigen to directly measure isotypes of antibodies to pathologically significant extracellular epitopes. These are pooled sera used in FIG. 4G, collected 6 months after initial immunization with *Torpedo* AChR with respect to FIG. 3, and after re-immunization with *Torpedo* AChR. After immunization with *Torpedo* AChR, normal rats primarily produced IgG2b antibodies. By contrast, IgG2b antibodies significantly decreased in the previously treated rats, while IgG1 antibodies, which are regulated by Th2 cells and do not fix complement, significantly increased after re-immunization with *Torpedo* AChR. (C) These are sera collected on day 36 in FIG. 3. Both EAMG control rats and rats treated with 1 mg of the therapeutic vaccine in IFA weekly primarily produced IgG2b antibodies, which are regulated by Th1 cells and fix complement. (D) These are sera collected on day 91 in FIG. 3. Six weeks after the last therapeutic dose, the IgG isotype profile of both groups remained similar.

FIG. 8. The sequence for human acetylcholine receptor proteins α1 (SEQ ID NO 1), β1 (SEQ ID NO 2), γ (SEQ ID NO 3), δ (SEQ ID NO 4), and ε (SEQ ID NO 5).

DETAILED DESCRIPTION OF THE INVENTION

Figure 1A:
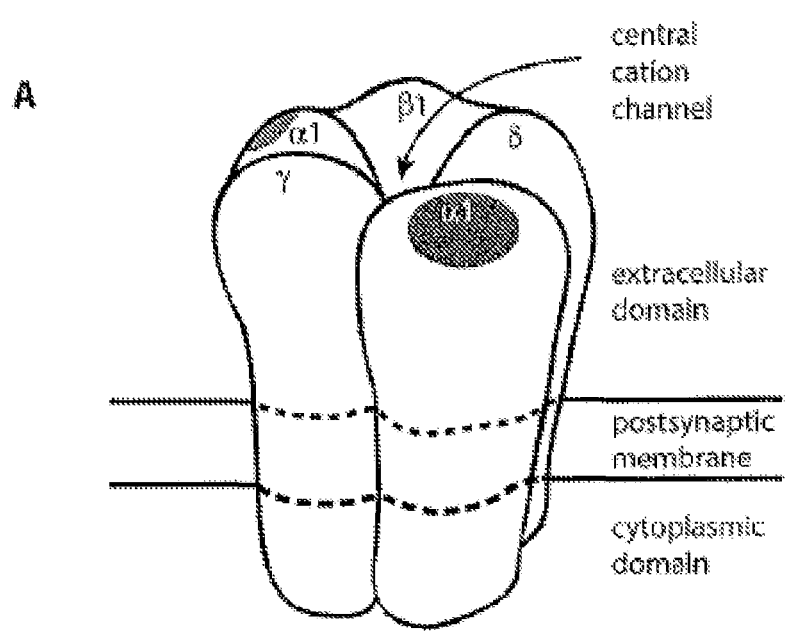
FIG. 1. Antibodies to AChR cytoplasmic domains did not passively transfer EAMG. (A) This depicts the structure of skeletal muscle AChRs. Five homologous subunits are organized like barrel staves around a central cation channel whose opening is triggered by binding of ACh to sites located in the extracellular domain at α1/δ and α1/γ subunit interfaces. Before innervation and after denervation y is replaced by ε. The areas in grey highlight the MIR which is located at the extracellular tip of a1 subunits and is the target of half or more of the autoantibodies to muscle AChRs in human MG and rat EAMG. (B) The two cytoplasmic domain proteins (5 μg each} were resolved by 10% SDS-PAGE and stained with SimpleBlue (Invitrogen, Carlsbad, Calif.), (C) IgG antibodies purified from rats repeatedly immunized with the cytoplasmic domains of human AChRs did not passively transfer EAMG (*$p<0.02$ relative to rats injected with mAb 35). Data represent the mean±SEM ($n=3$). The error bars, representing standard error, are too small to be seen.

The present invention generally relates to treatment of myasthenia gravis (MG) and, more particularly, to a vaccine for treatment of myasthenia gravis. The present invention more generally relates to treatment or therapy with one or more cytoplasmic domains of a transmembrane domain protein that is the object of an antibody-mediated autoimmune response.

Myasthenia gravis (MG) and its animal model experimental autoimmune myasthenia gravis (EAMG) are caused by an antibody-mediated autoimmune response to acetylcholine receptors (AChRs) of skeletal muscles that impairs neuromuscular transmission, resulting in weakness and fatigability. EAMG is induced by immunizing rodents or other species including primates with purified AChR. The specificities of pathological autoantibodies in MG and EAMG are similar. Half or more are directed at the main immunogenic region (MIR). Pathological mechanisms impairing neuromuscular transmission in MG and chronic EAMG are similar. Complement-mediated focal lysis of the postsynaptic membrane and antigenic modulation of AChRs disrupt the morphology of the synapse and reduce the number of AChRs. Therapy of MG with inhibitors of acetylcholine esterase to increase ACh to compensate for loss of AChRs and steroid and cytotoxic nonspecific immunosuppressive drugs are beneficial, but limited in efficacy and hampered by side effects. There is no cure for MG or therapy that specifically suppresses only the pathological autoimmune response to AChRs. We have devised a specific immunosuppressive therapy for EAMG that is effective at specifically suppressing the pathological autoimmune response to the extracellular surface of the AChR. It can rapidly inhibit ongoing chronic EAMG. This therapy involves immunization with the cytoplasmic domains of human AChR subunits expressed in bacteria. Incomplete Freund's adjuvant (IFA) may be used for therapeutic immunization. The therapy is potent, robust, long lasting, and likely to be free of the side effects of nonspecific immunosuppressive therapy. Reference is made to Luo J. and Lindstrom J., *J Immunology*, 2014, 193: 5044-5055 and Luo J and Lindstrom J (2015) *Biochem. Pharmacol.*, 2015, each of which is hereby incorporated by reference in its entirety for all purposes.

One benefit of the present invention is the use of non-pathological epitopes in treatment and/or alleviation of MG or EAMG. Another benefit of the present invention is the rapid effect on chronic EAMG or MG with long term beneficial effects. This approach to specific immunosuppressive therapy has the potential for application to antibody-mediated autoimmune responses to other transmembrane proteins.

Definitions

Unless defined otherwise, all technical and scientific terms used herein have the same meaning as commonly understood by one of ordinary skill in the art to which this invention belongs. Although any methods and materials similar or equivalent to those described herein can be used in practice or testing of the present invention, the preferred methods and materials are described.

As used herein, each of the following terms has the meaning associated with it in this section.

The articles "a" and "an" are used herein to refer to one or more than one (i.e., to at least one) of the grammatical object of the article. By way of example, "an element" means one lament or more than one element.

"About" as used herein when referring to a measurable value such as an amount a temporal duration, and the like, is meant to encompass variations of 20% or 10%, more preferably 5%, even more preferably 1%, and still more preferably 0.1% from the specified value, as such variations are appropriate to perform the disclosed methods.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab, and F(ab)$_2$, as well as single chain antibodies and humanized antibodies.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response can encode an "antigen" as that term is used herein. Furthermore, one skilled in the art will understand that an antigen need not be encoded fully by a full length nucleotide sequence of a gene. It is readily apparent that the present invention includes, but is not limited to, the use of partial nucleotide sequences of more than one gene and that these nucleotide sequences can be arranged in various combinations to elicit the desired immune response. Moreover, a skilled artisan will understand that an antigen need not be encoded by a "gene" at all. It is readily apparent that an antigen can be generated, synthesized or can be derived from a biological sample. Such a biological sample can include, but is not limited to a tissue sample, a tumor sample, a cell or a biological fluid.

A "disease" is a state of health of an animal, preferably a mammal and more preferably a human wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

An "effective amount" or a "therapeutically effective amount" of a compound is that amount of compound which is sufficient to provide a beneficial effect to the subject to which the compound is administered. An "effective amount" of a delivery vehicle is that amount sufficient to effectively bind or deliver a compound.

As used herein, the term "fragment," as applied to a protein or peptide, refers to a subsequence of a larger protein or peptide. A "fragment" of a protein or peptide can be at least about 20 amino acids in length, for example at least about 50 amino acids in length; at least about 100 amino acids in length, at least about 200 amino acids in length, at least about 300 amino acids in length, and at least about 400 amino acids in length (and any integer value in between).

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in the agglutination complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides, and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The terms "patient," "subject," "individual," and the like are used interchangeably herein, and refer to any animal, or cells thereof whether in vitro or in situ, amenable to the methods described herein. Preferably, the patient, subject, or individual is a mammal, and more preferably, a human.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

As used herein, "vaccination" is intended for prophylactic or therapeutic vaccination.

Throughout this disclosure, various aspects of the invention can be presented in range format. It should be understood that the description in the range format is merely for the convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3.7, 3, 4, 5, 6.3, and 6. This applies regardless of the breadth of the range.

Compositions

Figure 8:
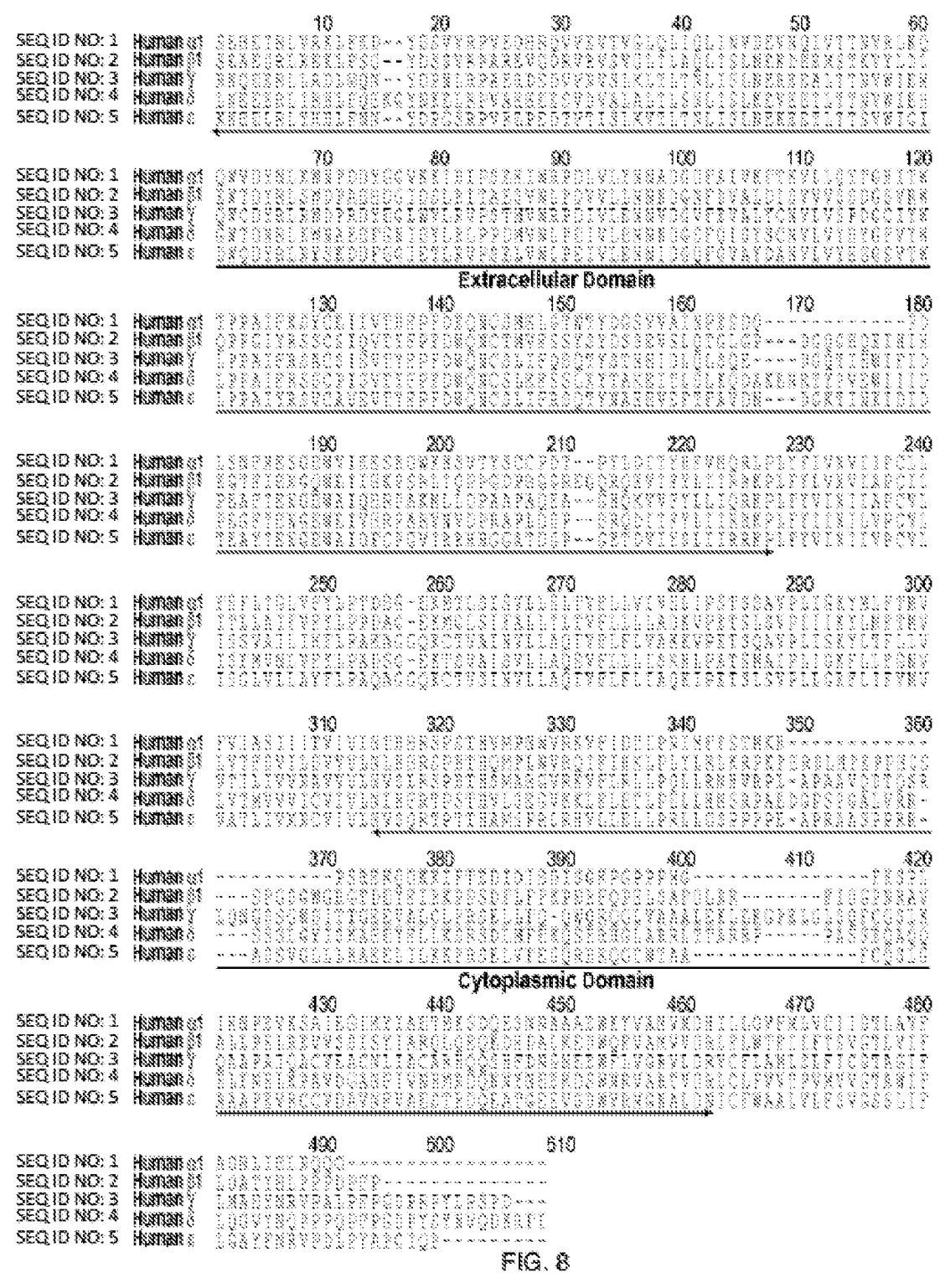

An aspect of the present invention provides a vaccine composition that is capable of alleviating or treating myasthenia gravis (MG) or experimental autoimmune myasthenia gravis (EAMG) in a patient suffering therefrom. The vaccine composition may comprise at least one acetylcholine receptor (AChR) subunit construct and an adjuvant. In some embodiments it is possible to immunize with a DNA segment that encodes at least one acetylcholine receptor (AChR) subunit as described herein, having greater than 75%, 80%, 85%, 90%, 95%, 98%, 99% identity with at least one AChR subunit sequences as described in Table 1 and FIG. 8, or fragments thereof.

In certain embodiments, a vaccine includes one, two or three or more AChR subunit constructs and an adjuvant. In some embodiments the AChR subunit construct is one or more of an AChR α1 subunit construct, an AChR β1 subunit construct, an AChR γ subunit construct, an AChR δ subunit construct, or an AChR ε subunit construct. The subunit construct can be of the extracellular domain, the large cytoplasmic domain, the C-terminal domain, functional portion, or any immunogenic combination or immunogenic fragment thereof. In some embodiments the subunit construct is of the cytoplasmic domain. The AChR subunit constructs may be of any mammal, for example, mouse, rat, cat, cow, pig, and in particular, human.

In some embodiments which include 2 or more subunit constructs, the ratio of a first subunit construct to a second subunit construct is 1:1, 1:2, 1:3, 1:4, 1:5, 1:6, 1:7, 1:10, 1:20, 1:30, 1:50 or 1:100. In some embodiments, the ratio of a first subunit construct to a second subunit construct is in the range of 1:1 to 1:100.

The sequences corresponding to certain subunit constructs for use with the present invention are shown in Table 1.

TABLE 1

TABLE 1: Human AChR Subunit Sequences Incorporated in Therapeutic Constructs

| | ExtracellularDomain | Large Cytoplasmic Domain | C-Terminal Domain |
|---|---|---|---|
| Subunit Constructs | | | |
| α1 | α1 1-209 | α1 297-408 | α1 428-437 + 6 his |
| β1 | β1 1-220 | β1 309-445 | β1 466-478 + 6 his |
| γ | γ 2-217 | γ 307-457 | γ 472-494 |
| δ | δ 2-224 | δ 313-450 | δ 469-496 |
| ε | ε 1-219 | ε 309-437 | ε 466-473 |
| Cytoplasmic Domain Constructs | | | |
| β1 α1γ | β1 310-446 | α1 297-408 | γ 307-451 |
| ε α1δ | ε 309-436 | α1 297-408 | δ 313-451 |

In some embodiments, the amino acid sequence of a subunit construct of an embodiment of the invention can be greater than 75%, 80%, 85%, 90%, 95%, 98%, 99% identical to the extracellular domain, the large cytoplasmic domain, the C-terminal domain, or any combination or fragment thereof of a sequence corresponding to a subunit such as those set forth in Table 1.

In some embodiments the vaccine further includes an adjuvant. Any pharmaceutically acceptable adjuvant may form a part of the invention. Pharmaceutically acceptable adjuvants include, but are not limited to Cationic liposome-DNA complex JVRS-100, aluminum hydroxide vaccine adjuvant, aluminum phosphate vaccine adjuvant, aluminum potassium sulfate adjuvant, Alhydrogel, ISCOM(s)™, Freund's Complete Adjuvant, Freund's Incomplete Adjuvant, non-methylated deoxyribonucleic acids containing CpG oligonucleotides, CpG DNA Vaccine Adjuvant, Cholera toxin, Cholera toxin B subunit, Liposomes, Saponin Vaccine Adjuvant, dimethyldioctadecylammonium bromide (DDA) adjuvant, Squalene-based Adjuvants, Etx B subunit Adjuvant, IL-1, IL-3, IL-6 and IL-12 Vaccine Adjuvant, LTK63 Vaccine Mutant Adjuvant, TiterMax Gold Adjuvant, Ribi Vaccine Adjuvant, Montanide ISA 720 Adjuvant, *Corynebacterium*-derived P40 Vaccine Adjuvant, MPL™ Adjuvant, AS04, AS02, Lipopolysaccharide Vaccine Adjuvant, muramyl peptide adjuvant, Muramyl Dipeptide Adjuvant, CRL1005, Killed *Corynebacterium parvum* Vaccine Adjuvant, Montanide ISA 51. *Bordetella pertussis* component Vaccine Adjuvant, Cationic Liposomal Vaccine Adjuvant, Adamantylamide Dipeptide Vaccine Adjuvant, Arlacel A, VSA-3 Adjuvant, Aluminum vaccine adjuvant, Polygen Vaccine Adjuvant, Adjumer™, Algal Glucan, Bay R1005, Theramide®, Stearyl Tyrosine, Specol, Algammulin, Avridine®, Calcium Phosphate Gel, CTA1-DD gene fusion protein, DOC/Alum Complex, Gamma Inulin, Gerbu Adjuvant, GM-CSF, GMDP, Recombinant hIFN-gamma/Interferon-g, interferon, Interleukin-1β, Interleukin-2, Interleukin-7 (IL-7), Sclavo peptide, Rehydragel LV, Rehydragel HPA, Loxoribine, MF59, MTP-PE Liposomes, Murametide, Murapalmitine, D-Murapalmitine, NAGO 1, Non-Ionic Surfactant Vesicles, PMMA, Protein Cochleates, QS-21, SPT (Antigen Formulation), nanoemulsion vaccine adjuvant, AS03 (a mixture of squalene, α-tocopherol, and polysorbate 80), Quil-A vaccine adjuvant, RC529 vaccine adjuvant, LTR192G Vaccine Adjuvant, *E. coli* heat-labile toxin, LT, amorphous aluminum hydroxyphosphate sulfate adjuvant, Calcium phosphate vaccine adjuvant, Montanide Incomplete Seppic Adjuvant, Imiquimod, Resiquimod, AF03, Flagellin, Poly(I:C), ISCOMATRIX®, Abisco-100 vaccine adjuvant, Albumin-heparin microparticles vaccine adjuvant, AS-2 vaccine adjuvant, B7-2 vaccine adjuvant, DHEA vaccine adjuvant, Immunoliposomes Containing Antibodies to Costimulatory Molecules, SAF-1, Sendai Proteoliposomes, Sendai-containing Lipid Matrices, Threonyl muramyl dipeptide (TMDP), Ty Particles vaccine adjuvant, Bupivacaine vaccine adjuvant, DL-PGL (Polyester poly (DL-lactide-co-glycolide)) vaccine adjuvant, Interleukin-15 (IL-15) vaccine adjuvant, LTK72 vaccine adjuvant, MPL-SE vaccine adjuvant, tumor necrosis factor, Cholera toxin B subunit, non-toxic mutant E112K of Cholera Toxin mCT-E112K, thimerosal, parrafin, non-ionic block polymer (NBP) adjuvant, and Matrix-S.

In certain embodiments, the adjuvant is pharmaceutically acceptable for use in humans. Currently, some pharmaceutically acceptable adjuvants that are acceptable in humans include, but are not limited to aluminum hydroxide vaccine adjuvant, aluminum phosphate vaccine adjuvant, aluminum potassium sulfate adjuvant, alhydrogel, AS04 (a combination of aluminum hydroxide and monophosphoryl lipid A), *Bordetella pertussis* component vaccine adjuvant, aluminum vaccine adjuvant, MF59, AS03, amorphous aluminum hydroxyphosphate sulfate adjuvant, sorbitan trioleate emulsified in squalene oil and Tween 80, and combinations thereof. In some embodiments the adjuvant comprises an aluminum salt. Aluminum salts that are suitable in adjuvants include, but are not limited to, aluminum hydroxide, aluminum phosphate, aluminum potassium sulfate, aluminum hydroxyphosphate sulfate.

In some embodiments the adjuvant or combination of adjuvants induces a Th2 response. In some embodiments the adjuvant induces a Th2 response that is greater than any Th1 response the adjuvant may induce.

In some embodiments the ratio of AChR subunit construct to adjuvant is about 1:10000 (mg/mL), about 1:9500 (mg/mL), about 1:9000 (mg/mL), about 1:8500 (mg/mL), about 1:8000 (mg/mL), about 1:7500 (mg/mL), about 1:7000 (mg/mL), about 1:6500 (mg/mL), about 1:6000 (mg/mL), about 1:5500 (mg/mL), about 1:5000 (mg/mL), about 1:4750 (mg/mL), about 1:4500 (mg/mL), about 1:4250 (mg/mL), about 1:4000 (mg/mL), about 1:3750 (mg/mL), about 1:3500 (mg/mL), about 1:3250 (mg/mL), about 1:3000 (mg/mL), about 1:2750 (mg/mL), about 1:2500 (mg/mL), about 1:2250 (mg/mL), about 1:2000 (mg/mL), about 1:1750 (mg/mL), about 1:1500 (mg/mL), about 1:1250 (mg/mL), about 1:1000 (mg/mL), about 1:950 (mg/mL), 1:900 (mg/mL), about 1:850 (mg/mL), about 1:800 (mg/mL), about 1:750 (mg/mL), about 1:700 (mg/mL), about 1:650 (mg/mL), about 1:600 (mg/mL), about 1:550 (mg/mL), about 1:500 (mg/mL), about 1:450 (mg/mL), about 1:400 (mg/mL), about 1:350 (mg/mL), about 1:300 (mg/mL), about 1:250 (mg/mL), about 1:200 (mg/mL), about 1:150 (mg/mL), about 1:100 (mg/mL), about 1:50 (mg/mL), or about 1:1 (mg/mL).

In some embodiments the ratio of AChR subunit construct to adjuvant is in a range of about 1:10000 (mg/mL) to about 1:9500 (mg/mL), about 1:9500 (mg/mL) to about 1:9000 (mg/mL), about 1:9000 (mg/mL) to about 1:8500 (mg/mL), about 1:8500 (mg/mL) to about 1:8000 (mg/mL), about 1:8000 (mg/mL) to about 1:7500 (mg/mL), about 1:7500 (mg/mL) to about 1:7000 (mg/mL), about 1:7000 (mg/mL) to about 1:6500 (mg/mL), about 1:6500 (mg/mL) to about 1:6000 (mg/mL), about 1:6000 (mg/mL) to about 1:5500 (mg/mL), about 1:5500 (mg/mL) to about 1:5000 (mg/mL), about 1:5000 (mg/mL) to about 1:4750 (mg/mL), about 1:4750 (mg/mL) to about 1:4500 (mg/mL), about 1:4500 (mg/mL) to about 1:4250 (mg/mL), about 1:4250 (mg/mL) to about 1:4000 (mg/mL), about 1:4000 (mg/mL) to about 1:3750 (mg/mL), about 1:3750 (mg/mL) to about 1:3500 (mg/mL), about 1:3500 (mg/mL) to about 1:3250 (mg/mL), about 1:3250 (mg/mL) to about 1:2000 (mg/mL), about 1:2000 (mg/mL) to about 1:1750 (mg/mL), about 1:1750 (mg/mL) to about 1:1500 (mg/mL), about 1:1500 (mg/mL) to about 1:1250 (mg/mL), about 1:1250 (mg/mL) to about 1:1000 (mg/mL), about 1:1000 (mg/mL) to about 1:750 (mg/mL), about 1:750 (mg/mL) to about 1:500 (mg/mL), about 1:500 (mg/mL) to about 1:250 (mg/mL), about 1:250 (mg/mL) to about 1:100 (mg/mL), or about 1:100 (mg/mL) to about 1:1 (mg/mL).

Methods of Preparing

An aspect of the present invention provides a method of preparing a vaccine composition comprising expressing one or more acetylcholine receptor subunit constructs in bacteria; purifying the one or more acetylcholine receptor subunit constructs; and combining the one or more acetylcholine receptor subunit constructs with an adjuvant in a pharmaceutically acceptable carrier (e.g., sterile water, saline, etc.). Methods for expressing the acetylcholine receptor subunit construct are described in Luo, J., A. Kuryatov, and J. M. Lindstrom. 2010 "Specific immunotherapy of experimental myasthenia gravis by a novel mechanism" *Ann Neurol* 67:441-451, which is incorporated by reference in its entirety and are described in Example 1 herein.

Embodiments of the present invention may also be used or combined with common formulations including emulsions (o/w and w/o), liposomes (including phospholipid), micellar lipid-saponin complexes, and PLG microspheres.

Methods of Treatment

An aspect of the present invention provides a method of treating a patient having myasthenia gravis (MG) or experimental autoimmune myasthenia gravis (EAMG) comprising administering a vaccine comprising an acetylcholine receptor subunit construct and an adjuvant to the patient, wherein the acetylcholine receptor subunit construct is selected from the group consisting of AChR $\alpha1$ subunit (SEQ ID NO 1), AChR $\beta1$ subunit (SEQ ID NO 2), AChR $\gamma$ subunit (SEQ ID NO 3), AChR $\delta$ subunit (SEQ ID NO 4), and AChR $\varepsilon$ subunit (SEQ ID NO 5), fragments thereof, and combinations thereof.

An aspect of the present invention provides a method of treating a patient having acute myasthenia gravis (MG) or acute experimental autoimmune myasthenia gravis (EAMG) comprising administering a vaccine comprising an acetylcholine receptor subunit construct and an adjuvant to the patient, wherein the acetylcholine receptor subunit construct is selected from the group consisting of AChR $\alpha1$ subunit (SEQ ID NO 1), AChR $\beta1$ subunit (SEQ ID NO 2), AChR $\gamma$ subunit (SEQ ID NO 3), AChR $\delta$ subunit (SEQ ID NO 4), and AChR $\varepsilon$ subunit (SEQ ID NO 5), fragments thereof, and combinations thereof.

Another aspect of the present invention provides a method of preventing the onset of chronic myasthenia gravis or chronic experimental autoimmune myasthenia gravis in a subject, comprising administering a vaccine comprising an acetylcholine receptor subunit construct and an adjuvant to the subject, wherein the acetylcholine receptor subunit construct is selected from the group consisting of AChR $\alpha1$ subunit (SEQ ID NO 1), AChR $\beta1$ subunit (SEQ ID NO 2), AChR $\gamma$ subunit (SEQ ID NO 3), AChR $\delta$ subunit (SEQ ID NO 4), and AChR $\varepsilon$ subunit (SEQ ID NO 5), fragments thereof, and combinations thereof.

The vaccine compositions of the present invention may be administered via a non-mucosal or mucosal route. These administrations may include in vivo administration via parenteral injection (e.g. intravenous, subcutaneous, and intramuscular), including the injection or implantation of depot formulations, or other traditional direct routes, such as buccal/sublingual, rectal, oral, nasal, topical (such as transdermal and ophthalmic), vaginal, pulmonary, intraarterial, intraperitoneal, intraocular, or intranasal routes or directly into a specific tissue. Alternatively, the vaccines of the invention may be administered by any of a variety of routes such as oral, topical, subcutaneous, mucosal, intravenous, intramuscular, intranasal, sublingual, transcutaneous, subdermal, intradermal, and via suppository. Administration may be accomplished simply by direct administration using a patch, needle, catheter or related device, a tablet, cream, gel, lotion, suppository, or spray.

The dose of vaccine formulation administered may depend on the route of administration chosen, the body weight of the patient, the blood volume of the patient, or other variables.

In some embodiments a dose of vaccine composition is about 0.01 ml, about 0.015 ml, about 0.02 ml, about 0.025 ml, about 0.03 ml, about 0.035 ml, about 0.04 ml, about 0.045 ml, about 0.05 ml, about 0.055 ml, about 0.06 ml, about 0.065 ml, about 0.07 ml, about 0.075 ml, about 0.08 ml, about 0.085 ml, about 0.09 ml, about 0.095 ml, about 0.1 ml, about 0.15 ml, about 0.2 ml, about 0.25 ml, about 0.3 ml, about 0.35 ml, about 0.4 ml, about 0.45 ml, about 0.5 ml, about 0.55 ml, about 0.6 ml, about 0.65 ml, about 0.7 ml, about 0.75 ml, about 0.8 ml, about 0.85 ml, about 0.9 ml, about 0.95 ml, about 1 ml, about 1.1 ml, about 1.2 ml, about 1.3 ml, about 1.4 ml, about 1.5 ml, about 1.6 ml, about 1.7 ml, about 1.8 ml, about 1.9 ml, about 2 ml, about 2.25 ml, about 2.5 ml, about 2.75 ml, about 3 ml, about 3.25 ml, about 3.5 ml, about 3.75 ml, about 4 ml, about 4.5 ml, about 4.75 ml, about 5 ml, about 10 ml, about 15 ml, about 20 ml, about 25 ml, about 30 ml, about 35 ml, about 40 ml, about 45 ml, about 50 ml, about 55 ml, about 60 ml, about 65 ml, about 70 ml, about 75 ml, about 80 ml, about 85 ml, about 90 ml, about 95 ml, or about 100 ml.

The amount of antigen in each antigenic or vaccine formulation dose is selected as an amount which reduces the amount of pathological antibodies without significant, adverse side effects. The measure of pathological antibodies may be assayed by titration of pathological antibodies to a $^{125}$I α1(1-32, 60-81)/AChBP chimera. The amount of antigen in each antigenic or vaccine formulation dose will vary depending upon which specific acetylcholine receptor subunit construct(s) is employed, route of administration, and adjuvants used. In general, the dose administered to a patient, in the context of the present invention should be sufficient to effect a beneficial therapeutic response in the patient over time, or to reduce the amount of pathological antibodies. Thus, a composition is administered to a patient in an amount sufficient to reduce the amount of pathological antibodies and/or to alleviate, reduce, or cure symptoms and/or complications from the disease or infection.

In some embodiments each dose may comprise about 0.001 mg to about 10 mg, 0.005 mg to about 8 mg, about 0.01 mg to about 6 mg, about 0.05 mg to about 4 mg, about 0.1 mg to about 2 mg, or about 0.5 mg to about 1.5 mg, or about 1 mg of acetylcholine receptor subunit construct(s).

In some embodiments, each dose may comprise about 0.001 mg, about 0.002 mg, about 0.003 mg, about 0.004 mg, about 0.005 mg, about 0.006 mg, about 0.007 mg, about 0.008 mg, about 0.009 mg, about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, 0.15 mg, about 0.2 mg, about 0.25 mg, about 0.3 mg, about 0.35 mg, about 0.4 mg, about 0.45 mg, about 0.5 mg, about 0.55 mg, about 0.6 mg, about 0.65 mg, about 0.7 mg, about 0.75 mg, about 0.8 mg, about 0.85 mg, about 0.9 mg, about 0.95 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg acetylcholine receptor subunit construct(s).

In some embodiments, each dose may comprise about 0.001 mg to about 10 mg, 0.001 mg to about 0.005 mg, about 0.005 mg to about 0.01 mg, about 0.01 mg to about 0.05 mg, about 0.05 mg to about 0.1 mg, about 0.1 mg to about 0.5 mg, about 0.5 mg to about 1 mg, about 1 mg to about 3 mg, about 3 mg to about 5 mg, or about 5 mg to about 10 acetylcholine receptor subunit construct(s).

Any of the above recited doses may be multiplied by a factor of 1, 2, 3, 4, 5 or 0.1, 0.01 or 0.001 to arrive at an actual administrable dose.

In a typical immunization regime employing the antigenic preparations of the present invention, the formulations may be administered in one or several doses (e.g. 1-6 or 1-4). The dose may be determined by the immunological activity the composition produces and the condition of the patient, as well as the body of the patient to be treated. The size of the dose also may be determined by the existence, nature, and extent of any adverse side effects that may accompany the administration of a particular composition in a particular patient.

Vaccine compositions of the invention may be administered at a single time point or at multiple time points. In some embodiments the dose may be administered several times a day, for example, five, four, or three times a day, twice a day, once a day, several times a week, for example, five, four, or three times a week, twice a week, once a week, several times a month, for example, five, four, or three times a month, twice a month, once a month, several times a year, for example, 12, 11, 10, 9, 8, 7, 6, 5, 4, or 3 times a year, twice a year, or once a year. In some embodiments where multiple doses are administered, the doses may be spaced regularly; in other embodiments where multiple doses are administered, the doses may be spaced irregularly.

In one embodiment one to six doses of the therapeutic vaccine, each including the same or different amount (in mg) of acetylcholine receptor subunit construct(s), is administered subcutaneously, once weekly for a duration to be determined by a caregiver. The amount of adjuvant can be determined based on the needs of the patient and the teachings described herein.

For example, in one embodiment six doses of the therapeutic vaccine, each including 0.25 mg acetylcholine receptor subunit construct(s), is administered subcutaneously, once weekly. In one embodiment six doses of the therapeutic vaccine, each including 0.5 mg acetylcholine receptor subunit construct(s), is administered subcutaneously, once weekly. In one embodiment six doses of the therapeutic vaccine, each including 1 mg acetylcholine receptor subunit construct(s), is administered subcutaneously, once weekly. In another embodiment three doses of the therapeutic vaccine, including 1 mg of acetylcholine receptor subunit construct(s) may be administered, one every two weeks. In another embodiment one dose of the therapeutic vaccine, including 0.5 mg of acetylcholine receptor subunit construct(s), is administered subcutaneously, followed by three boosts in IFA at three-week intervals Additional Information and Examples Additional Information and Examples can be found in the attached Appendix, which is to be considered part of this disclosure.

Example 1. Human AChR Subunit Constructs

Human AChR subunit constructs were engineered to remove the transmembrane domains and were cloned in the pET26(b) vector between Nde I and Xho I sites. Recombinant subunits were primarily present in inclusion bodies. These were solubilized using 3% sodium dodecyl sulfate (SDS) and 100 mM dithiothreitol (DTT) at 100° C., then purified on an AcA-34 Ultrogel sizing column (Sigma, St. Louis, Mo.). Purified subunits were concentrated by precipitation in 1.5 M NaCl at 0° C., then resolubilized in PBS. Remaining SDS was removed by dialysis. A mixture of α1, β1, γ, δ, and ε subunit constructs without transmembrane domains in a 2:1:1:1:1 weight ratio was used to treat ongoing EAMG.

In order to investigate therapy using only cytoplasmic domains, we expressed two contiguous cytoplasmic domain constructs. PCR products coding for the large cytoplasmic domain sequences were produced using the full-length subunit cDNA clones as a template. The upstream and downstream sequences of α1 were constructed to contain Spe I and BamH I restriction sites, respectively. The upstream and downstream sequences of β1 and ε were constructed to contain Nde I and Spe I sites, respectively. The upstream and downstream sequences of γ and δ were constructed to contain BamH I and Xho I sites, respectively. Primers for the PCR are listed in Supplementary Table 1. The purified PCR products were cut with the appropriate restriction enzymes. The fragments were ligated together and cloned in the pET26(b) vector between Nde I and Xho I sites to form two contiguous cytoplasmic domain constructs. One construct contained the cytoplasmic sequences of β1, α1, and γ in the order β1(310-446)-α1(297-408)-γ(307-451). The other contained the cytoplasmic sequences of ε, α1, and γ in the order ε(309-436)-α1(297-408)-δ(313-451). Together these two constructs reflect the order of subunits around the ion channel and provide the same stoichiometry used with constructs containing both extracellular and cytoplasmic domains. Recombinant proteins present in inclusion bodies were purified by the same approaches described above. A 1:1 weight ratio of the two cytoplasmic domain constructs were used to treat EAMG.

Figure 7A:
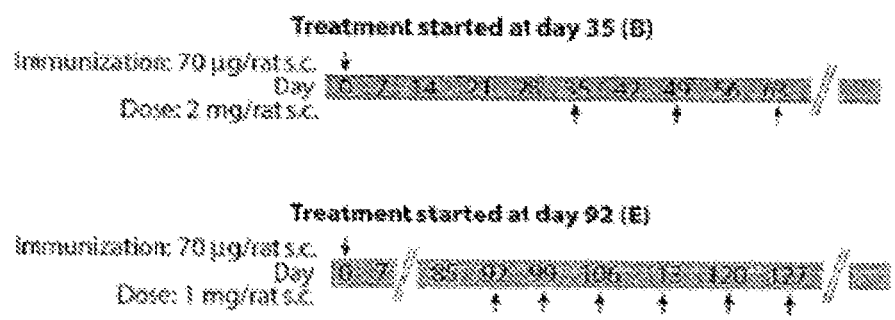
FIG. 7. Treatments started during the chronic phase rapidly suppressed further development of chronic EAMG and completely reversed weakness in most rats. (A) Immunization and treatment scheme. (B) When treatments started on day 35, the mean clinical scores of the treated rats were significantly lower compared to those of the untreated EAMG rats at all time points after day 43 (*$p<0.1$, **$p<0.05$). Data represent the mean±SEM (n=6). (C) Percentage of weight loss of these groups with respect to day 0. During the therapy period control EAMG rats lost more than 17% of body weight on average while treated rats lost less than 2% ($p<0.1$ after day 43, $p<0.05$ between days 49 and 63). (D) Equal amounts of sera from individual rats from 3 groups were pooled weekly after the acute phase of EAMG. Antibody titer of the pools to the MIR was evaluated as described in Materials and Methods herein. Treatments substantially reduced the titer to the MIR only one week after the first therapeutic dose. (E) When treatments started on day 92, the mean clinical scores of the treated rats were significantly lower compared to those of the untreated EAMG rats at all time points after. (F) Percentage of weight loss of these groups with respect to day 91 (one day before the treatment started). The treatment increased rat body weight by 25% on average, which is more than twice as much weight as the untreated and adjuvant control rats gained over the same period ($p<0.05$ between days 101 and 128, $p<0.1$ after day 128).
Figure 7B:
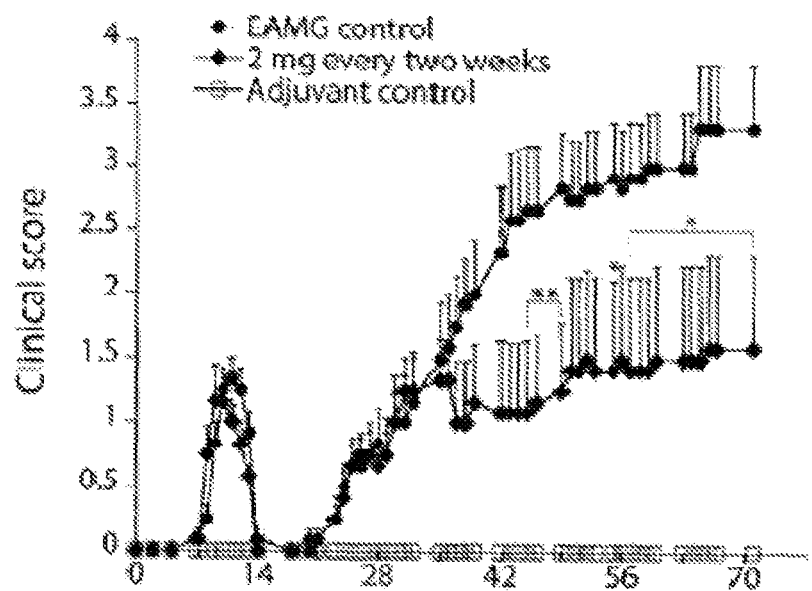

Purified proteins were analyzed by SDS-polyacrylamide gel electrophoresis (SDS-PAGE) and showed >99% purity.

muscle AChR as the antigen (FIG. 7B). When compared to the untreated EAMG rats, groups treated with either the subunit mixture or the cytoplasmic domain mixture had a higher proportion of the AChR-specific IgG1 (35% and 30% respectively, compared with 21% in untreated EAMG rats). IgG2b was significantly decreased in both treated groups (40% and 27% respectively, compared with 59% in untreated EAMG rats). However, a significant increase in IgG2a was detected in the rats treated with the cytoplasmic mixture. All groups had a minor proportion of the IgG2c isotype. Relatively limited changes in proportions of IgG1 and IgG2 isotypes (14% in the rats treated with the subunit mixture and 9% in those treated with the cytoplasmic mixture) are not sufficient to account for the extent of suppression of EAMG in the rats treated with either the subunit mixture or the cytoplasmic mixture.

A deviation from Th1 to Th2 regulation was proposed to be the mechanism of mucosal tolerance in rat EAMG. The selective polarization of IgG isotypes towards the Th2-regulated IgG1 was also observed in our treatments with either the subunit mixture or the cytoplasmic mixture. It has been reported that Th1 cytokines, but not Th2 cytokines, play a role in the development of EAMG in mice. Unlike in mice, there are arguments about whether the pathogenic humoral response is Th1-dependent in EAMG rats. Both AChR-specific Th1 and Th2 cells could be involved in rat EAMG. In human MG, the role of Th cell subsets is not yet established. However, indirect evidence indicates that both Th1 and Th2 subpopulations of T cells are involved in the autoimmune response in MG. Compared with mice, rat EAMG models are thought to be more relevant for the study of MG. Although AChR-specific T cells are required for

TABLE 2

Primer sequences used for PCR.

| Subunits | Sequences (5'-3') | SEQ ID No |
|---|---|---|
| α1 | F: ttcatcacta gtaacacaca ccaccgctca cccag | 6 |
| | R: aagagggatc cgtggtccat caccattgca acgtac | 7 |
| β1 | F: aattctacat atgcaccacc gctcacccca cac | 8 |
| | R: acacagacta gtgcggtcca ctaccatggc cacaaac | 9 |
| γ | F: tcaatggatc cttgcggtct ccacacacac ac | 10 |
| | R: atgaactcga ggcggtccag cactcggccc accagg | 11 |
| δ | F: tgataggatc ccacttccga acacccagca cccatgtgc | 12 |
| | R: aatatctcga ggcggtccac tgtgcgggcc act | 13 |
| ε | F: atactccata tgtcccagcg gacgcccacc ac | 14 |
| | R: aatatctcga ggcggtccac tgtgcgggcc act | 15 |

The effects of the i.p. treatments on humoral immune responses to AChR were investigated by analyzing AChR-specific IgG isotype profile in sera from the rats 7 weeks following disease induction. Antibodies directed to the recombinant constructs do not represent the autoantibody response toward native rat muscle AChR, because: 1) denatured recombinant constructs were not recognized by many pathologically relevant but conformation-dependent antibodies (treatment with the constructs provoked a large antibody response to themselves, but not to native AChR as shown above), and 2) we found that the IgG isotype profile of responses to the recombinant constructs was not parallel to that of autoimmune responses to rat muscle AChR (unpublished data). Thus, IgG isotypes were analyzed using rat EAMG development, the disease stems from the collaborative effects of T and B cells and subsequent activity of autoantibodies and complement. Both Th1- and Th2-regulated rat IgG isotypes are capable of binding complement. Both mAbs of IgG1 (e.g. mAb 35 and 210), IgG2a (e.g. mAb 42 and 198), and IgG2b isotype are potent at passive transfer of EAMG. Thus, the ability of mAbs to passively transfer EAMG depends on their binding specificity rather than their isotype.

Additional Material

Introduction

An antigen-specific therapeutic vaccine for MG could avoid side effects of nonspecific immunosuppressive drugs, such as infections and malignancies. Therapeutic vaccines using AChR extracellular domain sequences that form epitopes for pathological autoantibodies risk provoking autoimmunity rather than suppressing it. Bacterially-expressed human α1 subunit extracellular domain 1-210 can induce EAMG. Oral administration of human α1 1-205 extracellular domain peptide suppressed development of EAMG, but administering α1 1-210 exacerbated EAMG due to renaturation of the MIR. Removing two major B-cell epitopes from the human α1 1-210 fragment converted the pathogenic fragment into a therapeutic one. However, any extracellular antibody epitope is potentially pathogenic.

Cytoplasmic domains of the AChR are not accessible to autoantibodies in intact muscle (FIG. 1 A). Previously, we reported that a therapeutic vaccine consisting of bacterially-expressed cytoplasmic domains of human muscle AChR α1 (SEQ ID NO 1), β1 (SEQ ID NO 2), γ (SEQ ID NO 3), δ (SEQ ID NO 4), and ε (SEQ ID NO 5) subunits was more potent at suppressing EAMG than a vaccine with both extracellular and cytoplasmic domains because it excluded pathogenic epitopes. However, previous studies were limited to the prevention of chronic EAMG by starting the therapy after acute EAMG and before onset of chronic EAMG. There are large changes in immune status during the development of chronic EAMG. Autoantibody concentrations are small before onset of chronic EAMG: Autoantibody concentrations increase more than 20 fold during chronic EAMG. A therapy that exhibits immunosuppressive capacity when started before development of chronic EAMG may delay or lose its suppressive activity when the autoimmune cells are fully activated and long-lived plasma cells have matured. Treating preexisting chronic EAMG is most relevant to treating MG. The ideal therapy would be both antigen-specific and provide long-term or permanent protection against relapse. Here we show that vaccination in adjuvant with the therapeutic vaccine rapidly suppresses established chronic EAMG and provides long-term, possibly permanent resistance to re-induction of EAMG. This approach could provide the long awaited "cure" for MG.

Materials and Methods

Induction of EAMG. Eight-week-old female Lewis rats (Charles River, Wilmington, Mass.) were used according to principles outlined in the National Institutes of Health (NIH) Guide for the Care and Use of Laboratory Animals. Studies were approved by the Institutional Animal Care and Use Committee (IACUC) of the University of Pennsylvania. EAMG was induced by a single subcutaneous (s.c.) injection of purified *Torpedo californica* AChR emulsified in Titer-Max adjuvant (CytRx, Norcross, Ga.) at the base of the tail. Weakness was graded between 0 and 4 as follows: 0) healthy normal rats with no signs of EAMG; 1) mildly decreased activity and weak grip with fatigability; 2) weakness, hunched posture at rest, decreased body weight and tremor; 3) severe generalized weakness, marked decrease in body weight, II moribund; 4) dead. The rapidly progressing chronic weakness of EAMG induced by *Torpedo* AChR can be lethal before therapy can inhibit and reverse the pathology because of significant dehydration and body weight loss, which is a result of muscle weakness and the resulting problems with eating and drinking A soft dietary supplement (DietGel 76A, Clear$H_2O$, ME) was provided during the chronic phase of EAMG to minimize inhibition of eating and drinking due to muscle weakness, allowing more time for the therapy to work before the weakness becomes lethal.

Antigen preparation. Two contiguous cytoplasmic domain constructs, containing the large cytoplasmic domains of human muscle AChR β1 (SEQ ID NO 2), α1 (SEQ ID NO 1), and γ (SEQ ID NO 3) subunits and those of human muscle AChR ε (SEQ ID NO 5), α1 (SEQ ID NO 1), and δ (SEQ ID NO 4) subunits respectively, were bacterially expressed and chromatographically purified as described previously. Together these two constructs reflect the order of subunits around the ion channel (FIG. 1A): A human MIR chimera α1 (1-32, 60-81)/AChBP (MIR/AChBP) was expressed in tissue culture and chromatographically purified.

mAbs.

All subunit-specific mAbs used here have been characterized and described previously. mAb 35 and mAb 210 are directed at the MIR of AChR α1 subunit. All mAbs were purified from tissue culture supernatants by protein G affinity chromatography.

Antibody Assay.

Antibodies to AChRs and to the MIR were measured by immunoprecipitation of 1 nM of $^{125}$I-α bungarotoxin ($^{125}$I-α Bgt) labeled AChRs and $^{125}$1-MIR/AChBP chimera, respectively. Serially diluted rat sera were incubated with $^{125}$I-α Bgt labeled AChRs or $^{125}$I-MIR/AChBP chimera overnight at 4° C., followed by precipitation using goat anti-rat IgG for 3 hrs at room temperature. Immediately before centrifugation, samples were diluted to 1 ml with 0.5% Triton X-100 in phosphate buffered saline (PBS), pH 7.4. The pellets were then washed with 1 ml 0.5% Triton X-100 in PBS prior to a second centrifugation. The washed pellets were assayed by y counting. Titers were expressed as nmol of toxin binding sites bound or nmol of chimera bound per liter serum (nM). All measurements were in triplicate.

ELISA.

Antibodies to the therapeutic AChR cytoplasmic domains were assayed by ELISA as described previously. Microliter plates (Corning, Lowell, Mass.) were coated overnight at room temperature with 100 μl of the constructs (20 μg/ml in 0.1 M sodium carbonate buffer, pH 9.6). After blocking with 3% (w/w) of BSA and washing, 1001-11 serially diluted rat sera were added for 2 hrs at 37° C. Bound antibodies were detected using biotinylated goat anti-rat IgG and horseradish peroxidase (HRP) labeled streptavidin (Kirkegaard & Perry Laboratory, Gaithersburg, Md.). HRP activity was measured with QuantaBlu Fluorogenic Peroxidase Substrate Kit (Pierce, Rockford, Ill.). Titer is defined as the serum dilution that gives half-maximal binding. All measurements were in triplicate.

IgG Isotyping.

Anti-MIR IgG isotypes were assayed as previously described with minor modifications, by using microliter plates (Corning, Lowell, Mass.) coated with 100 μl of human MIR/AChBP chimera (20 μg/ml in 0.1 M sodium carbonate buffer, pH 8.8). After blocking with 3% BSA and washing, rat sera diluted with normal rat serum to a final anti-MIR titer of 0.3 nM were added and incubated overnight at 4° C. After three washes, HRP conjugated goat antisera to rat IgG isotypes (Bethyl Laboratories, Montgomery, Tex.) diluted Ill 000 in phosphate buffered saline (PBS), pH 7.4, were added for 4 hrs at 37° C. Bound antibodies were detected using the QuantaBlu Fluorogenic Peroxidase Substrate Kit (Pierce, Rockford, Ill.). All measurements were in triplicate.

Antigenic Modulation.

Antigenic modulation of AChRs on the H9c2 cell line (ATCC CRL 1446), a rat cell line that expresses muscle AChR, was assayed by incubation with 2 microliters of rat sera overnight in 24-well tissue culture plates (Corning, Lowell, Mass.) in Dulbecco's Modified Eagle Medium (DMEM) supplemented with I 0% fetal bovine serum (FBS) and 1% penicillin/streptomycin. Antigenic modulation, measured as loss of $^{125}$I-αBgt binding sites, was determined after 3 hrs incubation with 5 nM $^{125}$I-αBgt. Background radioactivity was determined using a 100-fold excess of unlabeled αBgt. Normal rat serum was used as negative control to determine the total amount of surface AChRs. All measurements were in triplicate. Percent loss of surface AChR by antigenic modulation was calculated as follows: % loss of surface AChR=(1−Δcpm in the presence of antisera/Δcpm in the presence of normal serum)×100. All measurements were in triplicate.

Passive Transfer of EAMG.

Pooled sera, purified IgGs, or mAbs to the MIR were injected i.p. into 8-week-old female Lewis rats (Charles River, Wilmington, Mass.) at time 0. Rats were examined every 12-24 hrs for weight loss, muscular weakness and fatigability, and scored as described above.

Complement Consumption.

Serum samples were exposed to 56° C. for 6 min to inactivate contaminating complement prior to use. Normal rat serum was used as a homologous complement source to estimate the complement activating capacity of antigen-antibody complexes. Serial dilutions of serum samples were mixed with a constant concentration of excess MIR/AChBP chimera and incubated at 4° C. overnight. Thereafter, equal volumes of diluted normal rat serum were added. The mixture was incubated at 37° C. for 60 min, and residual complement activity was determined using the Complement CH50 Assay Kit (HaemoScan, Groningen, Netherlands) according to manufacturer's instructions. Complement activity consumed by immune complexes formed between MIR/AChBP chimera and anti-MIR antibodies was expressed as the percentage of the available activities in normal rat serum. All measurements were in triplicate.

Statistics.

Differences between two groups were assessed with the unpaired Student's t test using a two-tailed distribution. All results are given as means±SEM. Results were considered statistically significant when P<0.05.

Results

Therapeutic Vaccine Induced Antibodies to Rat Muscle AChR but not EAMG.

Figure 1B:
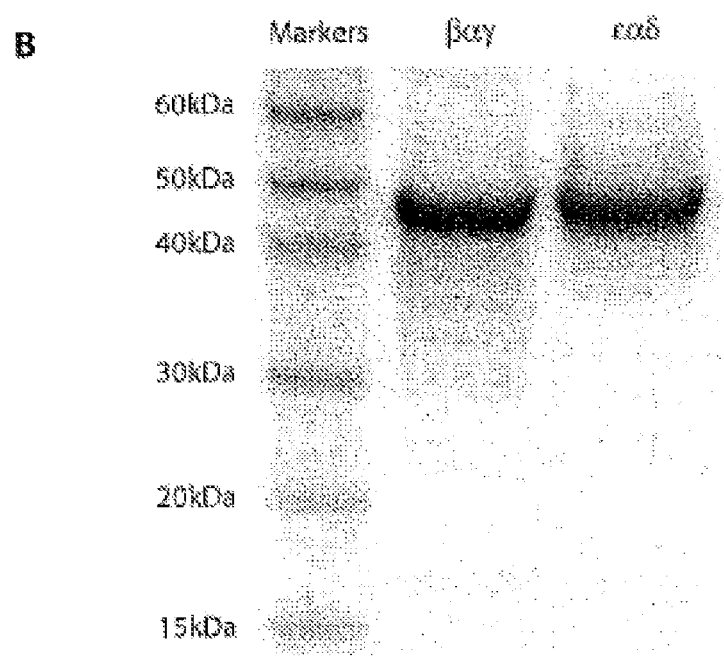

Purity of the two cytoplasmic domain components of the therapeutic vaccine was verified by SDS-PAGE (FIG. 1B). The two cytoplasmic domain constructs were combined in the weight ratio of 1:1 to be used in the following experiments.

Figure 1C:
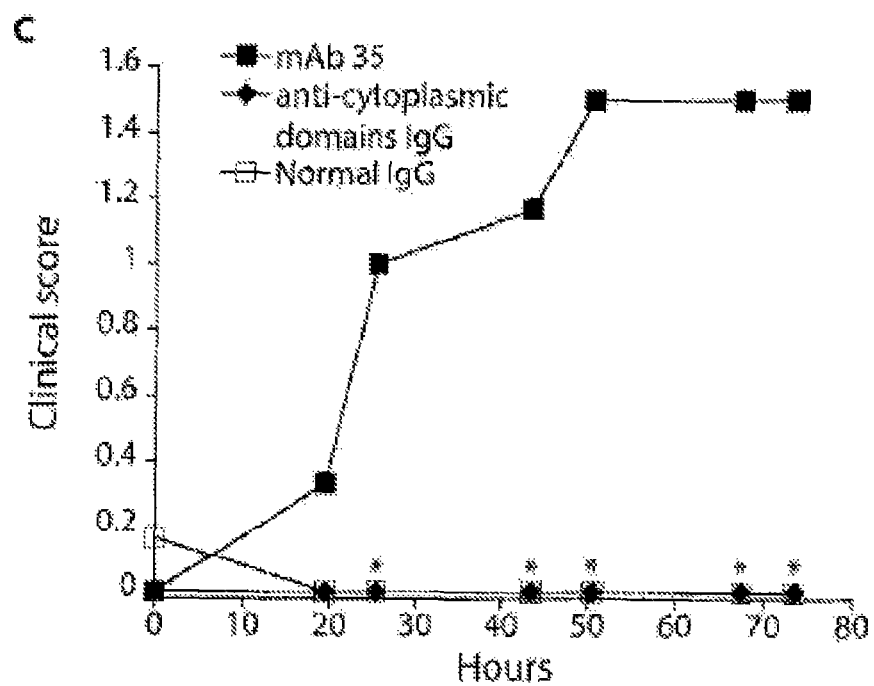

Immunization of rats with 0.5 mg of cytoplasmic domains in TiterMax adjuvant followed by three boosts in IFA at three-week intervals resulted in high titers of antibodies to rat muscle AChR (243 nM) but no signs of muscle weakness (mean clinical score 0 throughout the experiment and no loss of weight due to weakness). Lack of cross-reaction with the 1251 alpha 1(1-32, 60-81)/AChBP (MIR/AChBP) chimera indicates that antibodies are directed only against pathologically irrelevant epitopes on the cytoplasmic domains of rat muscle AChR. IgG antibodies were purified by Protein G Sepharose affinity chromatography from pooled serum of these rats. Three rats per group were injected i.p. with 1 mL of purified IgG (8 mg/ml) containing 186 pmol of autoantibodies to rat muscle AChR at time 0, then examined every 12-24 h for weight loss, muscular weakness and fatigability (FIG. 1C). 8 mg of IgG purified from normal rat serum was used as negative control. 113 pmol of mAb 35, a mAb to the MIR, was injected as positive control. Autoantibodies from rats immunized with the AChR cytoplasmic domains did not passively transfer EAMG. IgG purified from these rats failed to cause antigenic modulation of AChRs on H9c2 cells, a rat cell line that expresses muscle AChR. These results support the conclusion that immunization with AChR cytoplasmic domains induces no pathological autoantibodies.

Adjuvants Greatly Enhanced Therapeutic Potency.

Figure 2A:
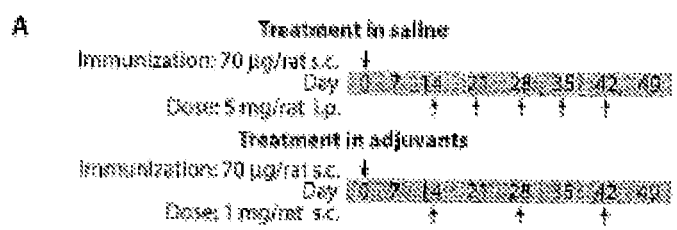
FIG. 2. Potency of the therapeutic vaccine was greatly increased by emulsion with IFA and changing the route of administration. (A) Immunization and treatment scheme. (B) Mean clinical scores of both the rats injected i.p. with 5 mg in saline and those injected s.c. with 1 mg in IFA were significantly lower than those of EAMG control rats at all time points after day 28 (both $p<0.01$). Mean clinical scores of the rats given injections s.c. first in TiterMax and then in IFA were lower than those of the EAMG control rats, but the difference is significant only at the 0.1 level ($0.1>p>0.05$ after day 28). Mean clinical scores of the rats given every injection in TiterMax were lower than those of EAMG control rats, but the difference is smaller than the other treatments ($0.2>p>0.05$ after day 28). Data represent the mean±SEM ($n=6$). (C) Equal amounts of sera from individual rats from 6 groups were pooled 7 weeks after the induction of EAMG. Antibody titer to the MIR was evaluated as described in Materials and Methods. Treatments reduced antibody titer to the MIR by around half, except weekly treatment with 1 mg/dose in IFA reduced titer to the MIR by a factor of 5. (D) Antibody titer to rat muscle AChR was evaluated as described in Materials and Methods. Treatment with 5 mg/dose in saline had little effect on autoantibody titer to rat muscle AChR, while all treatments with the vaccine emulsified in adjuvants significantly increased autoantibody titers by about 5 fold relative to untreated EAMG.
Figure 2B:
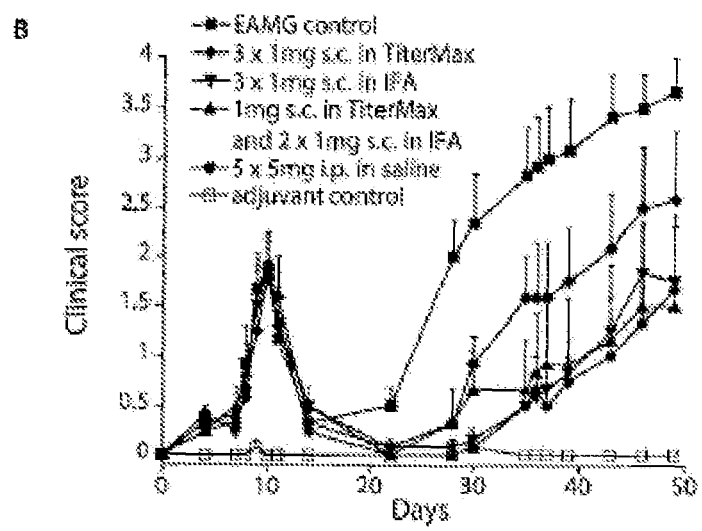

Potency of therapeutic vaccination with cytoplasmic domains at inhibiting the onset of chronic EAMG was greatly increased by adjuvants. All rats, except adjuvant controls which received equal volume of PBS emulsified in TiterMax adjuvant, were immunized with 70 μg of *Torpedo* AChR emulsified in TiterMax at day 0. After the acute phase of EAMG, these rats were grouped so that both clinical score and body weight distributions were similar between groups and mean clinical score and average body weight of each group were nearly equal. EAMG control rats received no treatment. Therapy was initiated after the acute phase, 14 days after induction of EAMG. Therapy consisted of 1 mg of therapeutic vaccine in adjuvants s.c. in four sites at the base of the tail every other week or six weeks. (FIG. 2A). As a comparison, a group of rats received 5 mg/dose i.p. in saline once a week for 5 weeks. This was the most effective dose and route of vaccination used in. our initial report that AChR cytoplasmic domains were more effective therapeutically than a combination of extracellular and cytoplasmic domains. Seven weeks after EAMG induction, all six untreated EAMG rats were weak, and five died of EAMG (mean clinical score 3.7) (FIG. 2B). In the group treated with 1 mg in IFA, 216 showed no weakness and only one died (mean clinical score 1.8). In the group treated with 5 mg in saline intraperitoneally (i.p.) weekly, 2/6 did not show clinical signs of EAMG, and 2 died (mean clinical score 1.7). One mg in IFA every other week for six weeks (3 mg total) was as effective as 5 mg in saline weekly for five weeks (25 mg total). Thus, IFA increased potency at reducing development of the weakness of chronic EAMG by 8 fold.

Figure 2C:
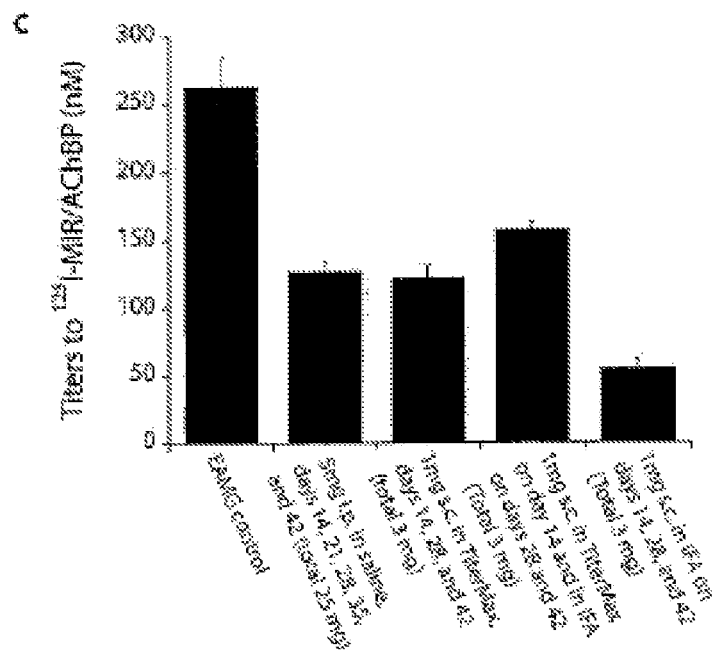
Figure 2D:
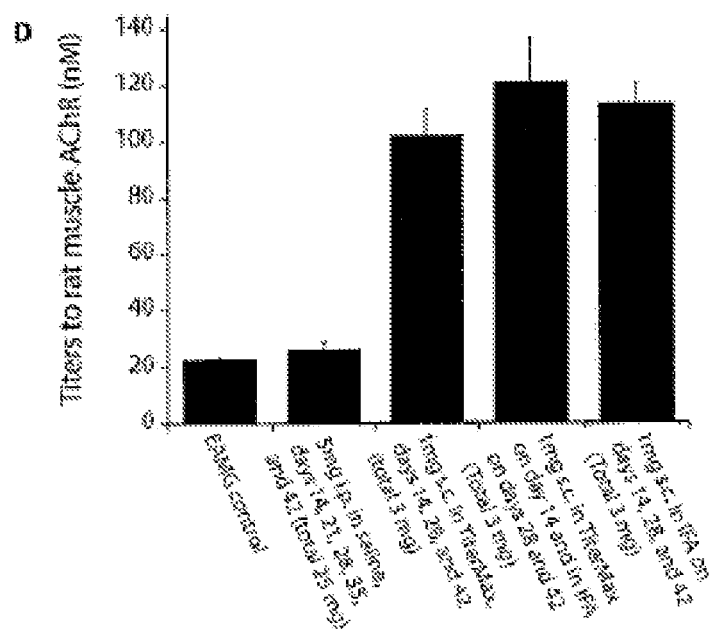

Treatment in IFA reduced the titer of pathological autoantibodies to $^{125}$I MIR/AChBP chimera 5 fold (FIG. 2C). Using TiterMax adjuvant for the first treatment was nearly as effective as using IFA at reducing weakness, but less effective at reducing the antibody titer to the MIR/AChBP chimera. Using TiterMax for every therapeutic injection was much less effective. Treatment with the therapeutic vaccine in either IFA or TiterMax increased antibodies to native rat muscle AChR 5 fold (FIG. 2D). Most autoantibodies to rat muscle AChR in treated rats are directed at pathologically irrelevant cytoplasmic epitopes because the titer to $^{125}$I MIR/AChBP chimera in these rats was reduced at least by half with respect to untreated EAMG (FIG. 2C). Amount of antibodies to the MIR was positively correlated with severity of weakness, while amount of antibodies to rat muscle AChR, including primarily antibodies to cytoplasmic domains, was negatively correlated with weakness.

Optimizing Vaccine Dose and Immunization Schedule Prevented Development of Chronic EAMG.

Efficacy of specific immunosuppressive therapy at inhibiting the onset of chronic EAMG was further improved by optimizing the dose and schedule of therapeutic vaccine in IFA. All rats, except adjuvant controls, were immunized with 70 μg of *Torpedo* AChR in TiterMax at day 0. After the acute phase, these rats were grouped so that both clinical score and body weight distributions were similar between groups and mean clinical score and average body weight of each group were nearly equal. Treatments for EAMG consisted of 6 s.c. doses of the therapeutic vaccine once weekly (0.25, 0.5, or 1 mg/dose) or 3 s.c. doses of 1 mg of the therapeutic vaccine once every two weeks starting on day 14

Figure 3A:
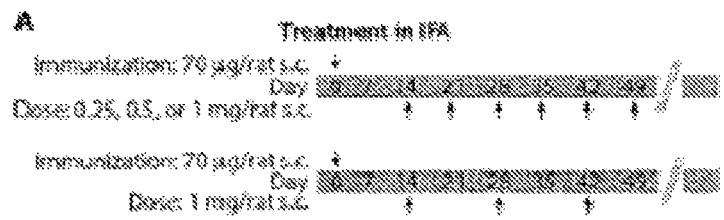
FIG. 3. Dose and schedule for specific immunosuppression using the therapeutic vaccine in IFA were further optimized. (A) Immunization and treatment scheme. (B) Mean clinical scores of the rats treated with 0.25 or 0.5 mg weekly were significantly lower than those of the untreated EAMG rats at all time points after day 56 ($p<0.05$). Mean clinical scores of the rats treated with 1 mg every other week were even lower ($p<0.05$ after day 44). Treatment with 1 mg in IFA weekly eliminated chronic weakness almost completely ($p<0.001$ relative to the untreated EAMG rats after day 42). Data represent the mean±SEM ($n=6$). (C) Percentage of weight loss of these groups with respect to day 0. All therapeutic doses except 0.25 mg weekly gained weight ($p<0.05$ for 1 mg at two-week intervals, $p<0.001$ for 1 mg weekly, versus untreated EAMG rats after day 44). (D) Equal amounts of sera from individual rats from 6 groups were pooled weekly after the induction of EAMG. Antibody titer of the pools to the MIR was evaluated as described in Materials and Methods. No cross-reaction was detected with $^{125}$I wild-type AChBP. Some error bars are too small to be seen. All treatments substantially suppressed the production of antibodies to the MIR three weeks after starting the treatments. Treatment with 1 mg weekly in IFA was most effective. (E) Sera of individual rats at day 36 were assayed for antibodies to the MIR. Treatment with 1 mg weekly in IFA significantly reduced the production of antibodies to the MIR ($p<0.05$ relative to the untreated EAMG rats). (F) Antibody titer of the pools to Torpedo AChR was evaluated as described in Materials and Methods. All doses of therapeutic vaccine suppressed antibody titer to Torpedo AChR similarly. (G) All doses of therapeutic vaccine rapidly increased antibody to AChR cytoplasmic domains to similarly high titers. The effect lasted for at least 6 weeks after the last therapeutic dose.

(FIG. 3A). EAMG control rats received equal volumes of an emulsion of PBS and IFA weekly. Each group consisted of six rats.

Figure 3B:
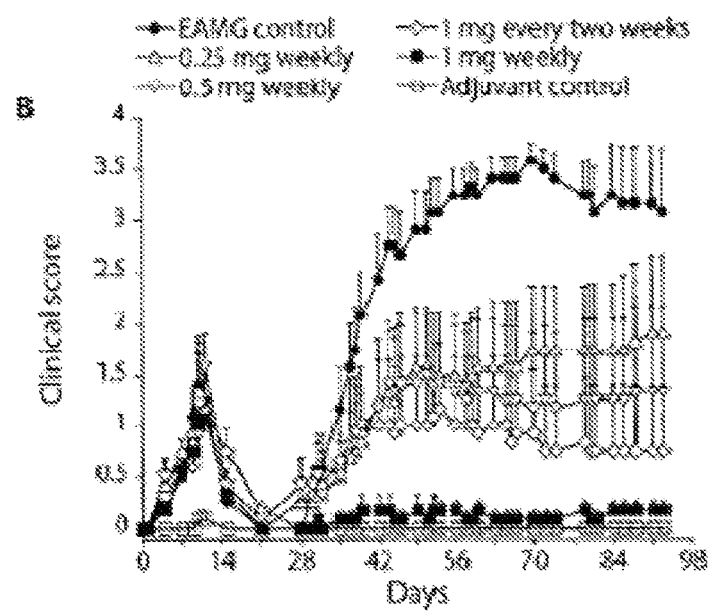
Figure 3C:
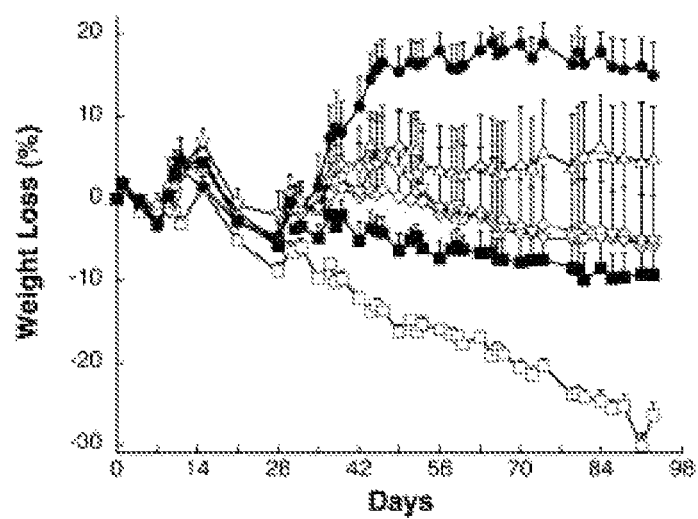
Figures 3D, 3E:
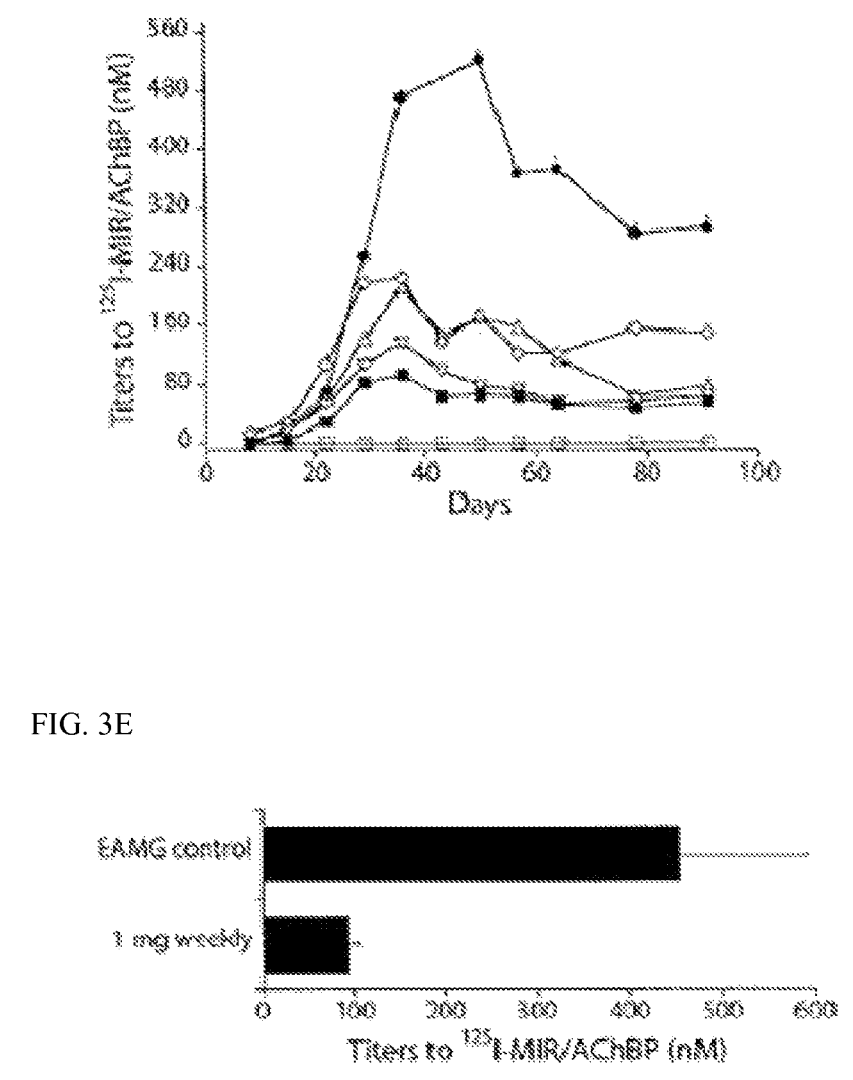
Figure 3F:
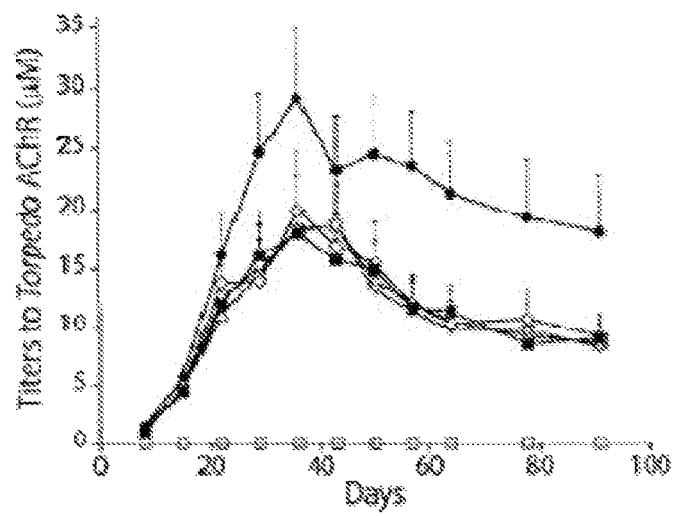

Therapeutic benefit was dose-dependent, with 1 mg in IFA at weekly intervals between days 14 and 49 (6 mg total) the most beneficial, eliminating chronic weakness almost completely (FIG. 3B). Five out of six rats showed no clinical signs of EAMG. One rat was transiently affected (peak clinical score 1). Thirteen weeks after disease induction, all 6 rats were healthy. By contrast, 6 untreated EAMG rats given IFA only were severely weak, and 4 died by 12 weeks (mean clinical score 3.6 at day 70). Lower doses were also beneficial. Overall, only 5 out of 24 treated rats from all 4 treatment groups died of EAMG by 12 weeks. All therapeutic doses except 0.25 mg weekly gained weight ($p<0.05$ for 1 mg at two-week intervals, $p<0.001$ for 1 mg weekly, versus untreated EAMG rats after day 44) (FIG. 3C).

Most of the surviving rats were retained for studies of the long-term effects of therapy. Fourteen weeks after induction of EAMG, 2 untreated EAMG rats and 4 rats treated with low doses that still showed signs of weakness were euthanized for ethical reasons. The remaining 15 rats were maintained for another 16 weeks. Three rats were euthanized because of infection unrelated to EAMG. All remaining rats continued without signs of weakness for an additional 23 weeks after the last therapeutic dose.

Treatment diverted autoantibody specificities away from pathological extracellular epitopes like the MIR.

Therapy initiated immediately after the acute phase decreased antibodies to the MIR two weeks after the first dose (FIGS. 3, D and E). One day after the last therapeutic dose (day 50), the most effective treatment (1 mg in IFA weekly between days 14 and 49) reduced the antibody titer to the MIR by a factor of 8 relative to untreated EAMG. Even six weeks later, the level of antibodies to the MIR in these rats was only 20% of that in untreated EAMG rats. All therapeutic doses reduced antibody titer to *Torpedo* AChR by half on day 91 (FIG. 3F).

Figure 3G:
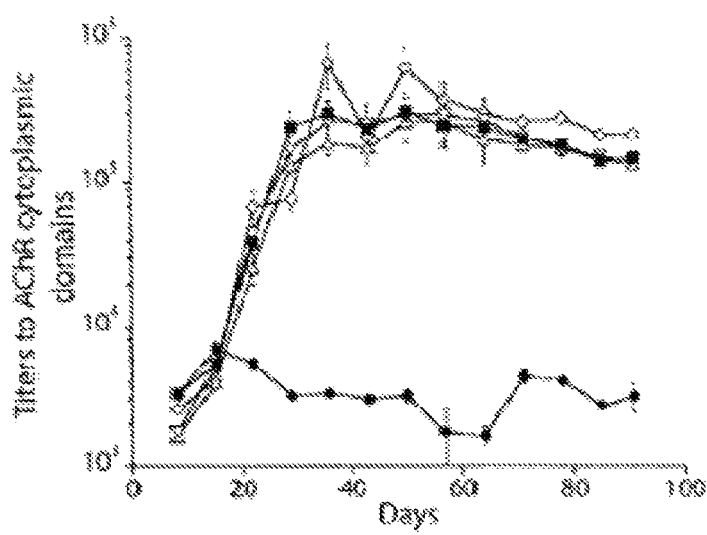

Vaccination increased the titer to therapeutic human AChR cytoplasmic domains up to 100 fold (FIG. 3G). These nonpathological antibodies also increased the titer to rat muscle AChR, as shown in FIG. 2D. Six weeks later, the titer to cytoplasmic domains in these rats was still 50 fold that of untreated EAMG rats.

Successfully treated rats were resistant to re-induction of EAMG.

Figure 4A:
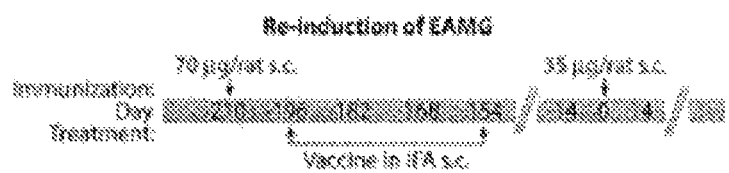
FIG. 4. Previously treated rats were resistant to re-induction of EAMG. (A) Immunization scheme. (B) The mean clinical scores of the rats previously treated then re-immunized with Torpedo AChR were significantly lower compared to those of the EAMG control rats at all time points after day 42 ($p<0.05$ between days 42 and 46, $p<0.01$ thereafter). Data represent the mean±SEM ($n=6$). (C) Percentage of weight loss of these groups with respect to day 0. Rats treated with any of the doses or schedules of therapeutic vaccine were significantly more resistant to re-induction of EAMG than control rats of the same age as measured by weight loss ($p<0.05$ after day 43). (D) All three groups of rats receiving mAb 210 were affected similarly ($p>0.37$). Data represent the mean±SEM ($n=3$). The error bars, representing standard error, are too small to be seen. (E) Equal amounts of sera from individual rats from 3 groups were pooled weekly after immunization. Antibody titer to Torpedo AChR was evaluated as described in Materials and Methods herein. Re-immunization with Torpedo AChR induced a big rise in antibody titer to the immunogen in the previously treated rats immediately after re-immunization. (F) Antibody titer to the MIR was evaluated as described in Materials and Methods herein Time course of antibody titer to the MIR paralleled that of titer to Torpedo AChR. (G) Two microliters of rat sera were incubated with H9c2 cells, and then antigenic modulation, measured as loss of aBgt binding sites, was determined. Sera from rats treated for EAMG and then immunized again with AChR were more potent at causing antigenic modulation. (H) Passive transfer of EAMG was tested using pooled serum aliquots (250 μl/rat). Data represent the mean±SEM ($n=3$). The error bars, representing standard error, are too small to be seen. Sera from the rats previously treated then re-immunized with Torpedo AChR caused no weakness, while those from EAMG control rats did ($p<0.05$). Rats injected with sera from the adjuvant control rats showed no weakness, as expected.
Figure 4B:
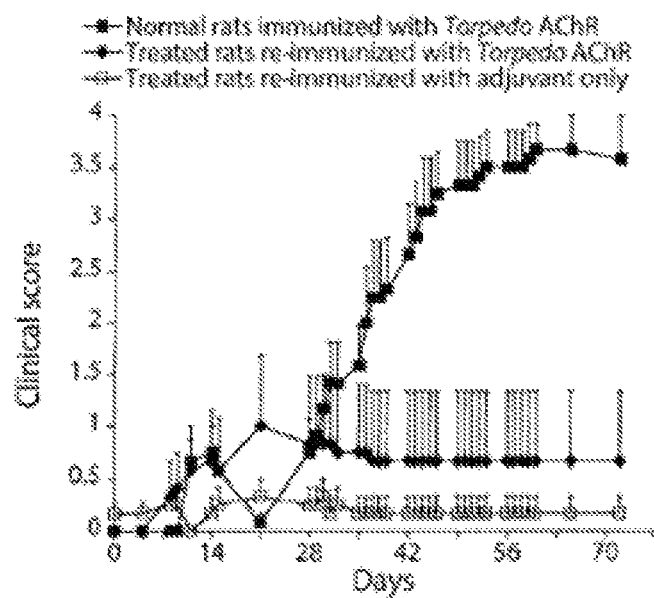
Figure 4C:
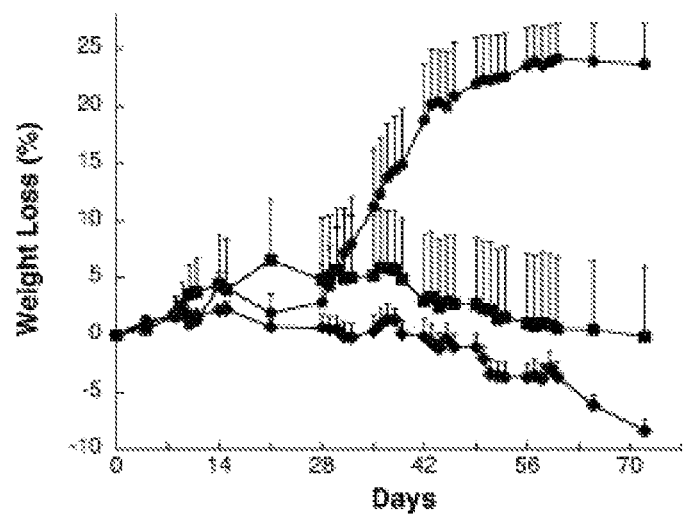

To determine whether treatment that prevented the onset of chronic EAMG prevented rats from relapse of EAMG, we tried to re-induce EAMG in successfully treated rats by immunizing them again with *Torpedo* AChR in TiterMax. Twenty-three weeks after the last therapeutic dose, twelve treated rats from FIG. 3 were randomly divided into two groups. One group was re-immunized with 35 μg of *Torpedo* AChR in TiterMax. The other group received an equal volume of PBS emulsified in TiterMax adjuvant. Six rats from the adjuvant control group in FIG. 3 were immunized with 35 μg of *Torpedo* AChR to form the EAMG control group (FIG. 4A). Treated rats were resistant to attempts to re-initiate EAMG by immunization with *Torpedo* AChR as measured by clinical state (FIG. 4B) or weight loss (FIG. 4C). Only 2/6 treated rats developed muscle weakness after the re-immunization. The others remained healthy throughout the experiment. The two weak rats did not have a typical biphasic course of EAMG. One of the weak rats died at day 21 and the other rat was moderately weak at that time (clinical score at day 21), then recovered two weeks later. Control rats of the same age were severely affected, developed typical biphasic EAMG, and 5/6 died after immunization with *Torpedo* AChR. Six previously treated rats used as adjuvant controls remained with little or no detectable weakness.

Successfully treated rats were as susceptible to passive transfer of EAMG by antibodies as were normal rats.

Figure 4D:
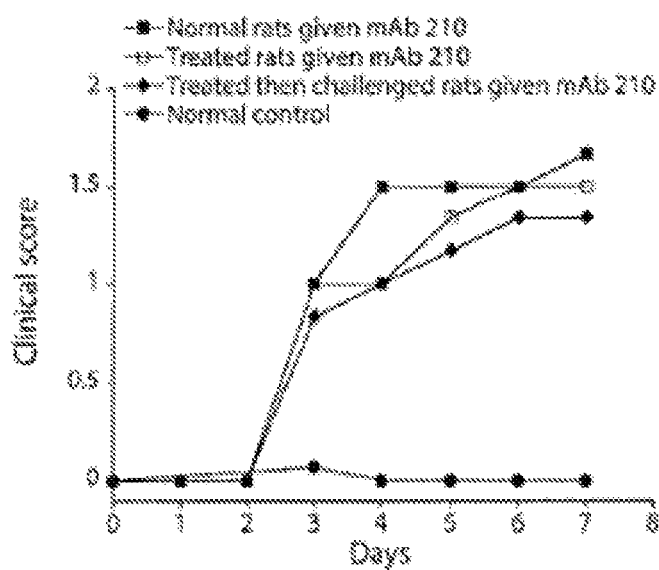

It has been reported that rats which recovered from passive transfer EAMG by autoantibodies to AChR became refractory to induction of EAMG by a second injection of autoantibodies. It was suggested that resistance to repeated passive transfer of EAMG resulted from low AChR amount or density in the postsynaptic membrane which was insufficient to initiate further AChR degradation. If our previously treated rats were resistant to re-induction of EAMG for this reason, these rats should also be resistant to passive transfer of EAMG by injection of a mAb to the MIR. Three previously treated then re-immunized rats, three previously treated rats from the adjuvant control group in FIG. 4B, and three normal rats at the same age were given i.p. 740 pmol/100 g body weight of anti-MIR mAb 210. Three normal rats at the same age were injected i.p. with normal rat IgG as negative control. Unlike young rats in which acute weakness usually peaks at day 2 after injection and clears within one week, these older rats showed signs of weakness after day 3 and stayed weak more than a week. All rats given mAb 210 developed acute EAMG of similar severity (FIG. 4D). Because previously treated rats were as susceptible to passive EAMG induced by mAb 210 as were normal rats, it is unlikely that the change of AChR amount or density in their neuromuscular junctions cause their resistance to re-induction of EAMG.

Treated rats developed no weakness after re-immunization with *Torpedo* AChR but made autoantibodies with pathological specifications.

Figure 4E:
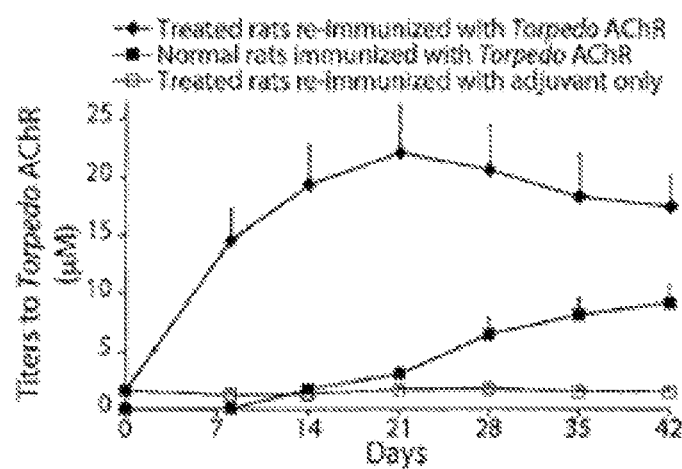
Figure 4F:
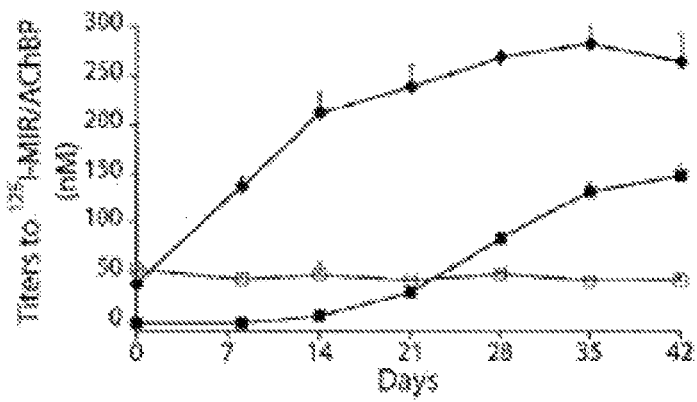

Re-immunization of treated rats with *Torpedo* AChR increased antibodies to both *Torpedo* AChR and the MIR, but not the therapeutic vaccine. Twenty-three weeks after the last therapeutic dose, previously treated rats, which were completely recovered, still had antibodies to *Torpedo* AChR (about 1.6 μM) and to the human MIR (about 40 nM). Titer to the therapeutic vaccine decreased by a factor of 4 relative to 23 weeks before, and remained unchanged after re-immunization with *Torpedo* AChR. Rats developed a strong antibody response to *Torpedo* AChR immediately after re-immunization with *Torpedo* AChR (FIG. 4E). Antibody to *Torpedo* AChR reached a peak of 22 μM on day 21. By contrast, control rats of the same age developed a modest response two weeks after immunization, and antibody to *Torpedo* AChR was only 3 μM by day 21. Time course of antibody titer to the MIR paralleled that to *Torpedo* AChR (FIG. 4F). Antibody to the MIR in previously treated rats was 8 fold higher than in normal rats by 21 days after immunization and 2 fold higher on day 42. The rapid and strong immune response of the previously treated rats after re-immunization with *Torpedo* AChR suggests that these rats developed memory B and T lymphocytes after the first immunization with *Torpedo* AChR.

Figure 4G:
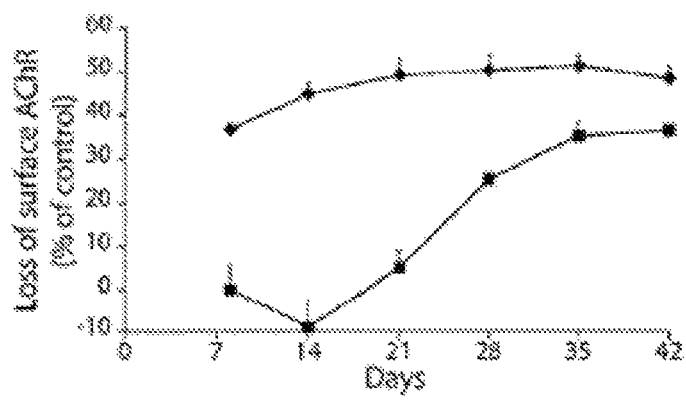

Antibodies in these sera that bind extracellular epitopes of rat muscle AChR were assayed by testing their ability to cause antigenic modulation of AChR on H9c2 cells. Sera from previously treated rats caused more antigenic modulation than did sera from control rats (FIG. 4G). After re-immunization with *Torpedo* AChR, previously treated rats developed more antibodies to the MIR than did control rats. However, despite the presence of autoantibodies with pathological specificities, only control rats developed severe EAMG.

Sera from treated rats could not passively transfer EAMG.

Pathogenicity of autoantibodies in the sera of the previously treated rats re-immunized with *Torpedo* AChR was compared with that of the autoantibodies in the sera of the same age control rats immunized with *Torpedo* AChR for the first time by testing their abilities to passively transfer EAMG.

Figure 4H:
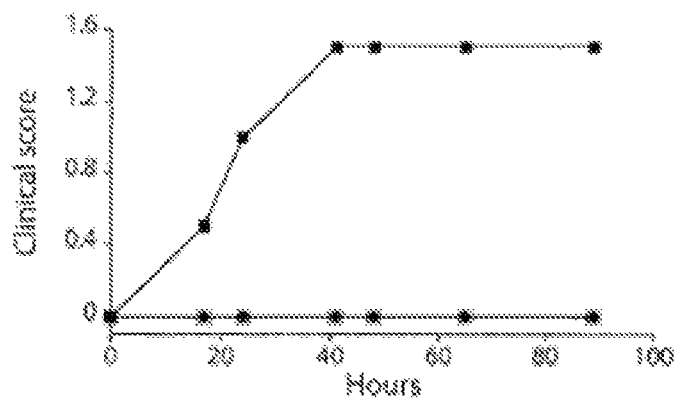

Three rats per group were injected i.p. with pooled serum aliquots (250 µl/rat) from the rats previously treated then re-immunized with *Torpedo* AChR, containing 67 pmol anti-MIR antibodies. Equal aliquots from the adjuvant control rats containing 12 pmol anti-MIR antibodies) and those from the EAMG control rats (containing 24 pmol anti-MIR antibodies) were injected as negative and positive controls, respectively. Sera from the previously treated rats were ineffective at passively transferring EAMG, while sera from the normal rats were effective (FIG. 4H). Autoantibodies from treated rats were less pathogenic, even though they contained more antibodies to the MIR and caused more severe antigenic modulation on H9c2 cells than those from normal rats. Thus, properties of antibodies from treated rats other than amount or specificity for pathologically significant epitopes were changed.

Isotype profile of anti-MIR antibodies was changed in treated rats after re-immunization with *Torpedo* AChR.

Figure 5A:
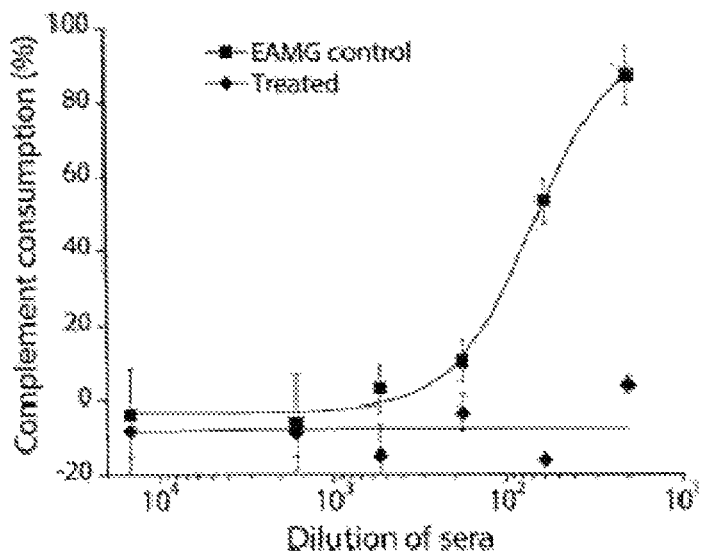
Figure 5B:
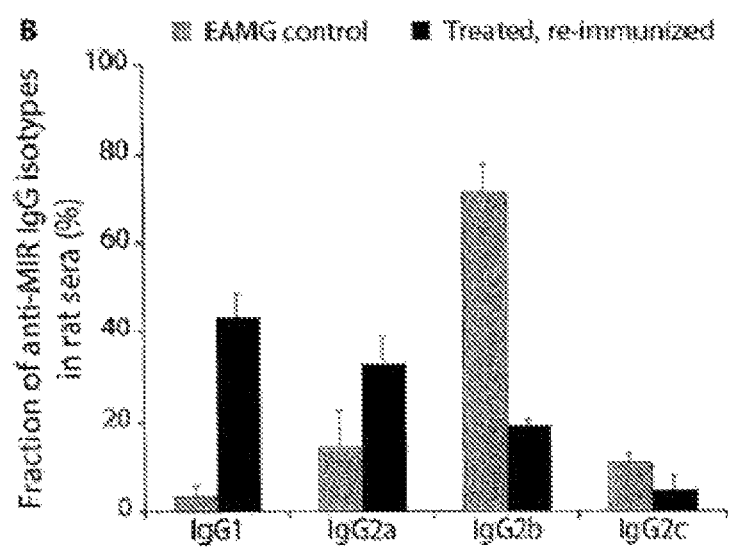
Figure 5C:
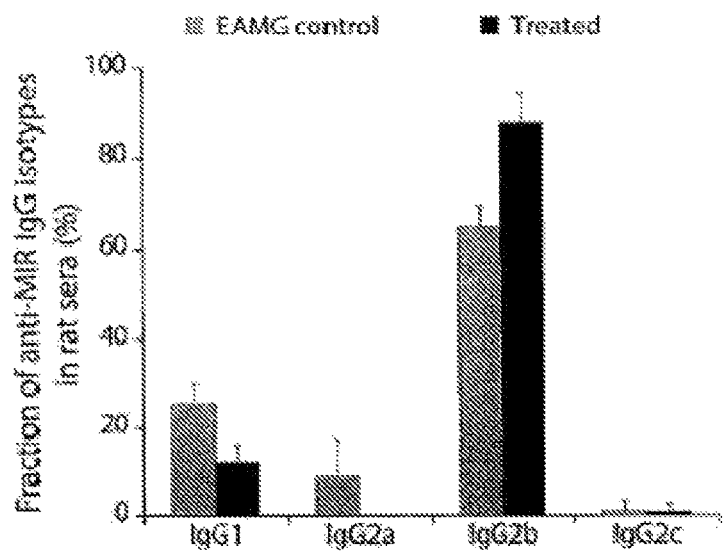
Figure 5D:
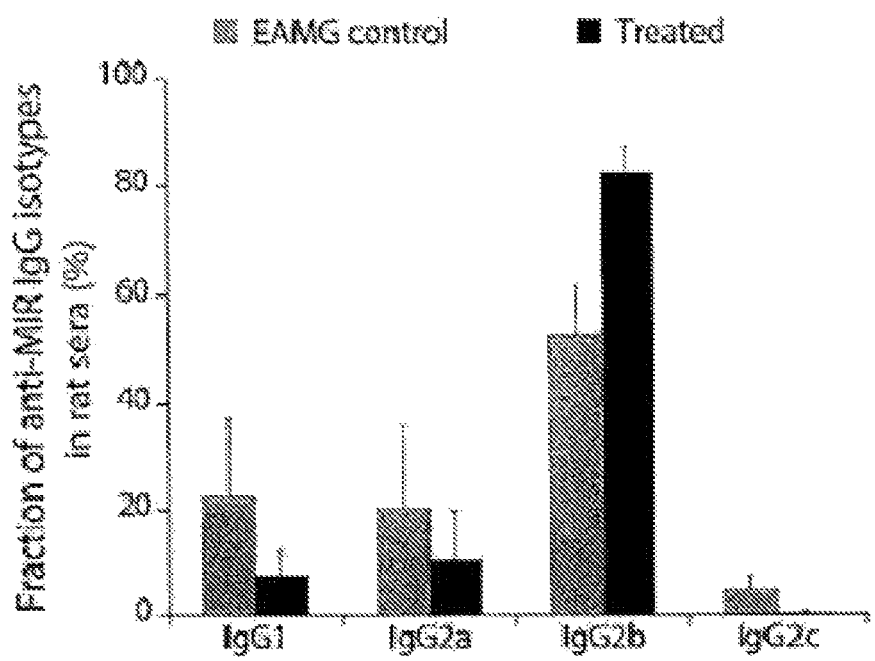

AChR loss caused by complement-mediated focal lysis is thought to be more pathologically significant than is accelerated AChR turnover by antibody cross-linking (antigenic modulation). Antibodies to the MIR from the rats initially immunized with *Torpedo* AChR were effective at fixing complement in response to binding MIR/AChBP chimera, while antibodies from rats treated for EAMG and later re-immunized with *Torpedo* AChR were not (FIG. 5A). Pathogenicity of antibodies depends on their ability to bind to AChRs in muscle and recruit complement. Not all lgG subclasses fix complement equally well. IgG2b has the greatest capacity, IgG2a is less efficient, and IgG1 has little capacity to fix complement. This reflects properties of the Fc region of lgG characteristic of each isotype. Analysis of isotypes of antibodies to the MIR revealed that IgG1 (regulated by Th2 cells in rats) grew from a minor fraction (3.5%) after initial immunization with *Torpedo* AChR to a major part (43.2%) in treated rats later re-immunized with *Torpedo* AChR. IgG2b (regulated by Th1 cells in rats) went from a predominant isotype (71.2%) in rats initially immunized with *Torpedo* AChR to a minor isotype (19.2%) in treated rats after later re-immunization with *Torpedo* AChR (FIG. 5B). Thus, serum antibodies from previously treated rats were less effective at fixing complement because of isotype switching.

To determine whether isotype switching occurred during or immediately after the previous therapy, the isotype profile of antibodies to the MIR in the sera from both EAMG control rats and treated rats in FIG. 3 was analyzed. Unlike after re-immunization with *Torpedo* AChR, IgG2b was still the predominant isotype in treated rats (87.7% on day 36 and 82.5% on day 91), as well as in untreated EAMG rats (64.8% on day 36 and 52.9% on day 91) (FIGS. 5, C and D). Thus, isotype switching is not an immediate cause of the benefit of therapy, but a long-term effect of therapy.

Untreated Rats Surviving EAMG were not Resistant Tore-Induction of EAMG.

Figure 6A:
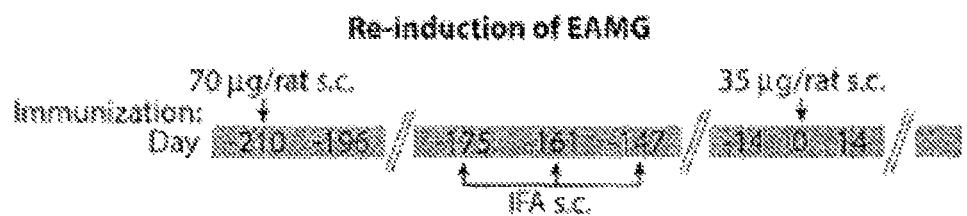
FIG. 6. Untreated rats that survived EAMG rapidly developed EAMG again when re-immunized with *Torpedo* AChR. (A) Immunization scheme. (B) The two surviving EAMG rats given adjuvant had little or no weakness. Both the adjuvant control rats and the surviving EAMG rats were severely weak after being immunized with *Torpedo* AChR. There is no significant difference in chronic EAMG between these two groups ($p>0.5$ after day 49). Data represent the mean±SEM. (C) Sera were collected 42 days after immunization. After immunization with *Torpedo* AChR, both normal rats and untreated EAMG rats mainly produced IgG2b antibodies, which are regulated by Th1 cells and fix complement.
Figure 6B:
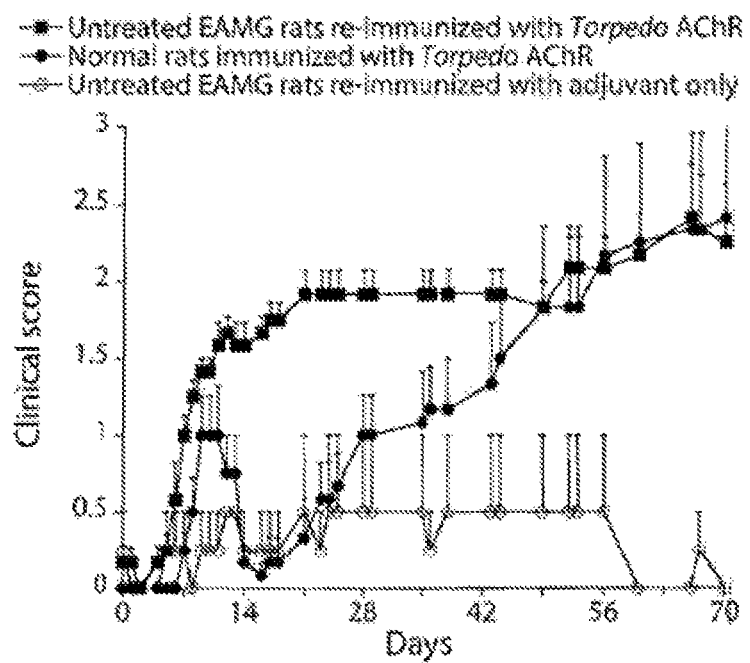
Figure 6C:
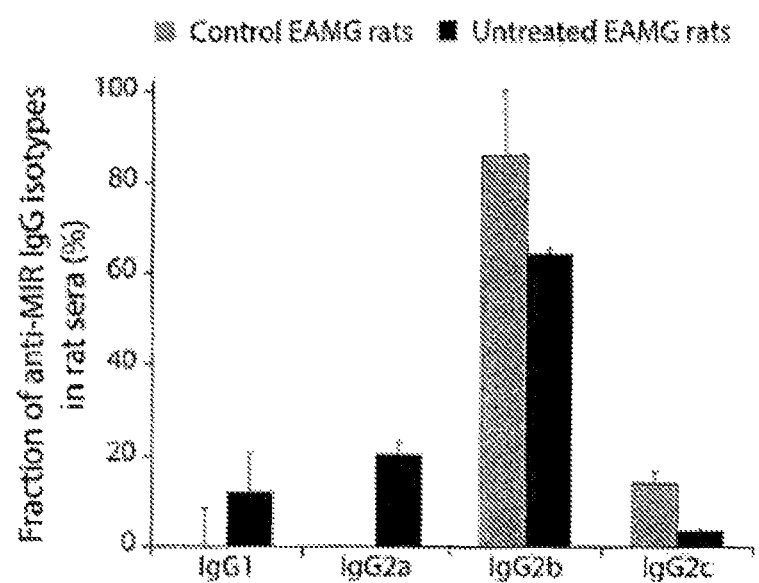

All untreated EAMG rats in FIG. 3 died of EAMG before re-induction of EAMG. Thus, the experiment of re-induction of EAMG, which was shown in FIG. 4, did not include a group of untreated EAMG rats. This raises the question of whether the resistance of the previously treated rats to re-induction of EAMG was a result of previous treatment, or a result of having survived EAMG. In order to answer this, 15 rats were immunized with 70 µg *Torpedo* AChR to induce EAMG and six rats of the same age received adjuvant only (FIG. 6A). These rats received 3 injections of an emulsion of PBS and IFA every other week started at day 35 after immunization. All rats immunized with *Torpedo* AChR developed EAMG. Thirty weeks after the initial immunization, eight rats that survived EAMG were still mildly fatigable, but all had gained weight and muscle strength. Their remaining antibody titer the MIR was approximately 74 nM. Six of the surviving untreated EAMG rats were immunized again with 35 µg '*Torpedo* AChR. Two others received adjuvant only as a negative control. Six rats that previously received adjuvant were immunized with 35 µg *Torpedo* AChR as an EAMG control. Unlike EAMG control rats of the same age, which developed typical biphasic EAMG after immunization with *Torpedo* AChR, untreated rats that had survived EAMG developed chronic EAMG only one week after re-immunization with *Torpedo* AChR (FIG. 6B). All six rats were severely affected (mean clinical score 2.3), and one died of EAMG. Five of six rats previously given adjuvant and then immunized with *Torpedo* AChR developed clinical weakness (mean clinical score 2.4). Two of them died. Thus, untreated EAMG rats did not show resistance to re-induction of EAMG. These rats developed a strong antibody response to the MIR immediately after re-immunization with *Torpedo* AChR. lgG2b-type antibodies were the major part of anti-MIR antibodies in these rats after re-immunization, just as after the initial immunization (FIG. 6C). Therefore, therapy, not having survived EAMG, shifted isotypes of antibodies to the MIR causing resistance to re-induction of EAMG in treated rats.

Treatment started during the chronic phase rapidly suppressed further development of chronic EAMG and returned most rats to normal.

Treatment with the therapeutic vaccine in IFA before onset of the chronic phase of EAMG can prevent chronic EAMG (FIG. 3A). The challenge in treating MG is beginning therapy during chronic MG. Unlike MG, which is usually much longer term and not so rapidly progressive, EAMG initiated with high doses of AChR usually produces rapidly progressing chronic weakness that is frequently lethal. Antibody titers to *Torpedo* AChR and to the MIR reached their peaks at day 35 after initial immunization (FIGS. 3, C and E).

Treatment of ongoing chronic EAMG with 3 doses of 2 mg of the therapeutic vaccines at 2-week intervals was effective (FIGS. 7, A and B). All rats except adjuvant control were immunized with 70 µg of *Torpedo* AChR in TiterMax at day 0. All rats immunized with AChR were treated with 3 mg/kg/day of pyridostigmine in their drinking water to provide symptomatic therapy. This drug is routinely used for symptomatic therapy in MG. The intent was to reduce weakness, thereby allowing more time for the treatment to work, and to accurately model how therapy would be used for MG. Immediately before starting treatment, the rats were grouped so that both clinical score and body weight distributions were similar between groups and mean clinical score and average body weight of each group were nearly equal. Treatment of EAMG. consisted of 3 doses of 2 mg of the therapeutic vaccine in IFA every two weeks starting on day 35 (6 mg total). EAMG control rats received injection s.c. of IFA at the same schedule. Relatively large (2 mg) doses were given with the intention of speeding the therapeutic effect before EAMG became lethal. Before starting treatment, 5/6 rats to be treated were sick (mean clinical score 1.3) and 4/6

Figure 7C:
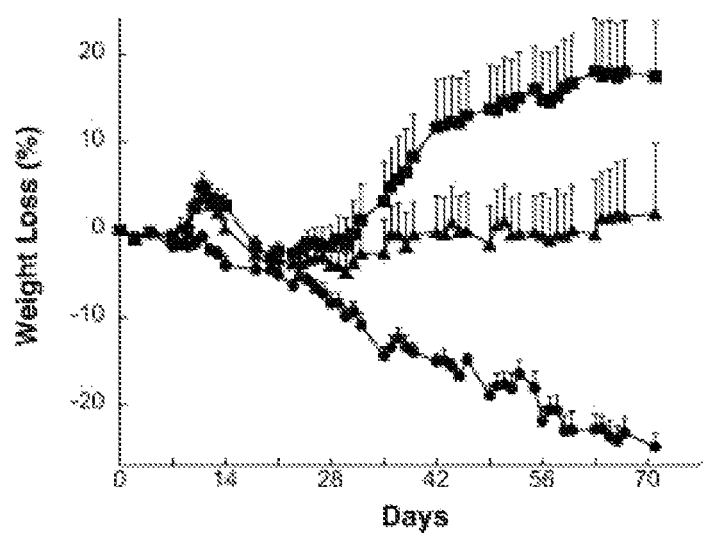
Figure 7D:
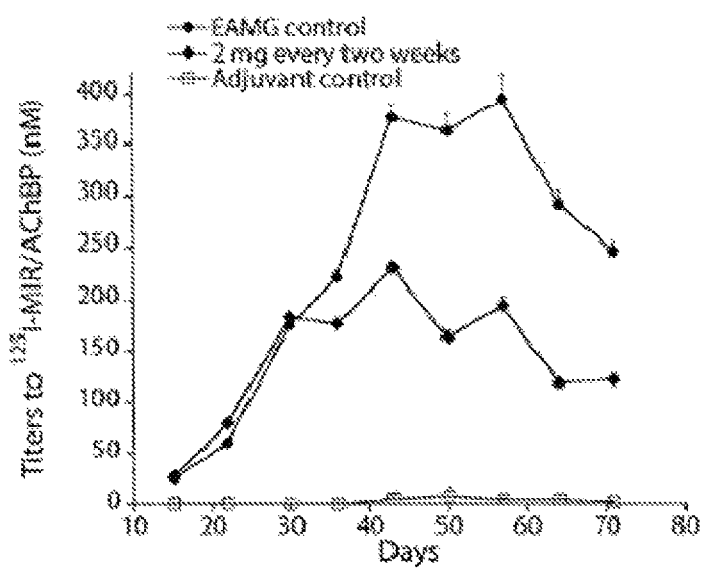
Figure 7E:
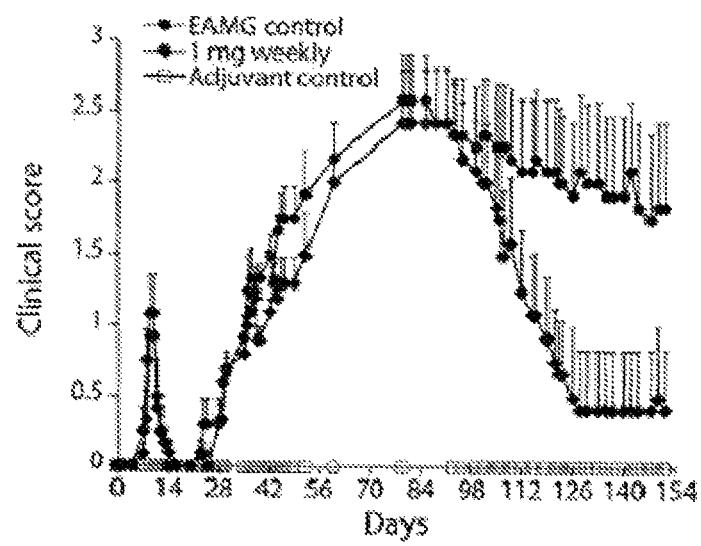
Figure 7F:
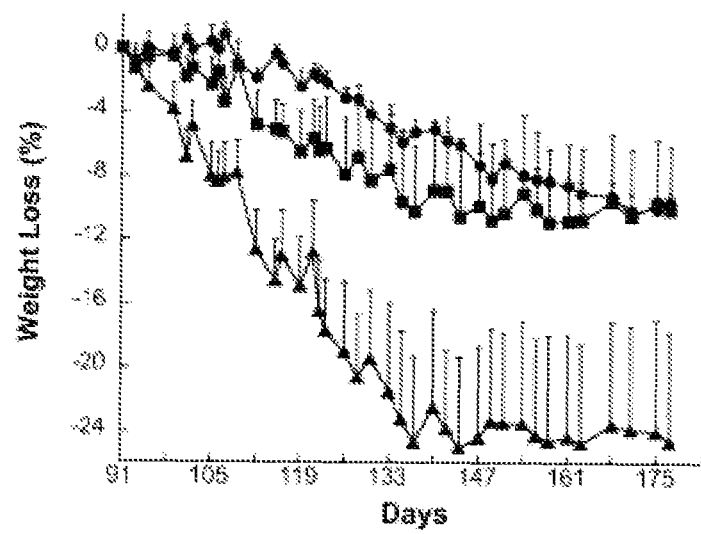

EAMG control rats were sick (mean clinical score 1.6). Effect of the treatment was rapid, but not so extensive as achieved when started before the chronic phase. By the end of the experiment, all six untreated rats with EAMG were weak and four rats were dead (mean clinical score 3.3), but 3/6 treated rats had returned to normal, and only one died (mean clinical score 1.6). The untreated rats lost an average of 29.8±11.9 grams during the treatment period. By contrast, the treated rats lost an average of 8.5±6.9 grams during the same period. Antibody titers to the MIR were almost identical between the two groups before starting treatment. Treatment suppressed the production of antibodies to the MIR by one week after the first dose. By the end of the experiment, antibody titer to the MIR was reduced by half relative to that in the untreated rats with EAMG (FIG. 7C).

Treatment of established chronic EAMG was highly effective with 6 doses of 1 mg of the therapeutic vaccine at 1 week intervals (FIGS. 7, A and D). Twenty-one rats were immunized with 70 µg Torpedo AChR to induce EAMG in order to provide a sufficient number of rats surviving long term chronic EAMG, and six rats received adjuvant only. All rats immunized with AChR were treated with 3 mg/kg/day of pyridostigmine in their drinking water to provide symptomatic therapy for weakness. Thirteen weeks after the initial immunization, fourteen rats (of the initial 21) survived EAMG. Twelve rats surviving EAMG were divided into two groups of 6 each so that the clinical scores and body weights of each group were similar. Before starting treatment, all rats in both groups were weak (mean clinical scores 2.4 in both groups). Six doses of 1 mg of the vaccine in IFA were given s.c. weekly starting on day 92 (6 mg total). EAMG control rats received injection s.c. of IFA at the same schedule. Effect of sustained lower dose therapy was rapid. After the last therapeutic dose, 5|6 treated rats recovered and exhibited no weakness, and only one was weak (mean clinical score 0.5). These treated rats gained an average of 32.2±6.7 grams over the 6-week treatment period. By contrast, 5/6 untreated EAMG rats were still weak at that time (mean clinical score 1.9). These rats gained an average of 14.8 grams during the same period. Thus, six weekly 1 mg doses in IFA was the most effective dose amount and schedule for both completely preventing development of chronic EAMG (FIG. 3B) and nearly completely suppressing long established chronic EAMG (FIG. 7D).

Discussion

We developed a specific immunosuppressive therapy for EAMG with great potential for treating MG. We demonstrated that a therapeutic vaccine using cytoplasmic domains of human AChR, α1 (SEQ ID NO 1), β1 (SEQ ID NO 2), γ (SEQ ID NO 3), δ (SEQ ID NO 4), and ε (SEQ ID NO 5) subunits is a safe and powerful tool for suppressing established EAMG and preventing relapse of EAMG. Cytoplasmic epitopes should not be pathogenic because of the inaccessibility of the cytoplasmic domains of AChR under physiological conditions. In fact, the vaccine is safe: 1) rats repeatedly immunized with the vaccine in adjuvants did not develop EAMG, although they produced antibodies which can bind to solubilized native AChRs; and 2) autoantibodies from these rats did not bind the MIR, passively transfer EAMG, or cause antigenic modulation. IFA greatly increased potency and efficacy of the therapeutic vaccine. Benefits of therapy are long lasting, possibly even permanent. Therapy for 6 weeks starting before onset of chronic EAMG prevented development of chronic EAMG, protected the rats from EAMG for at least 6 months afterwards, and protected the rats against relapse after a boost with Torpedo AChR 6 months later. This therapeutic regime started during chronic EAMG prevented further development of chronic EAMG and caused rapid improvement in most rats. Such effective therapy of chronic EAMG and prevention of relapse are unprecedented. Efficacy and safety recommend this therapeutic vaccine for further development in preparation for clinical testing for therapy of MG.

Most serum autoantibodies to AChR are produced by long-lived plasma cells residing in spleen and bone marrow. These terminally differentiated cells are resistant to most immunosuppressive drugs. Thus, there is typically a delay of up to 18 months after initiation of immunosuppressive therapy before MG patients improve. Antibody titer is low two weeks after induction of EAMG, when populations of plasma cells are minimal. Suppression of B cell differentiation would prevent further production of plasma cells. Treatment with 1 mg doses in IFA weekly starting at that time prevents muscle weakness. Even without treatment, antibody titer decreases gradually after it peaks 35 days after induction and spontaneous remissions occur around 90 days after induction, if rats have not died of EAMG. However, unlike treated rats, untreated rats that survived EAMG do not achieve a complete remission. This suggests that the B cell proliferation rate could be significantly decreased 90 days after induction and remaining long-lived plasma cells could play a crucial role in maintaining antibody level at that time. Treatment starting at day 92 rapidly reversed existing weakness. This suggests that our therapy could also inhibit or apoptose plasma cells. Apoptosis of plasma cells can be induced by Foxp3+Treg or by crosslinking FcγRIIb on the plasma cells by immune complexes. These mechanisms could explain the rapid effects of our therapy. This property of therapy precedes another clinically meaningful advantage over existing immunosuppressive therapy. Unlike MG, which is usually much longer term, EAMG induced with high doses of AChR usually produces rapidly progressing chronic weakness that is often fatal. Most deaths occurred between weeks 5 and 11 after induction. The observed resistance to therapy in some rats might be a result of irreversible damage caused by rapidly progressing extensive weakness. This adverse characteristic may not extend to human therapy.

Drachman and his colleagues tried to eliminate the autoimmune response in both EAMG and MG and provide long-term benefit by largely ablating the existing immune system with high dose cyclophosphamide. They found that some memory lymphocytes survive the treatment, and were required to prevent relapse in treated patients. Our antigen-specific immunotherapy resulted in rapid and durable improvement without dramatically altering the whole immune system. • When re-immunized with Torpedo AChR, treated rats developed an anamnestic antibody response that was apparently similar to that in untreated EAMG rats. However, unlike untreated EAMG rats which developed a Th1• regulated antibody response, treated rats primarily produced Th2 regulated antibodies that do not fix complement and thus are not pathogenic. Rather than "rebooting" the immune system, our• antigen-specific immunotherapy actually "reprograms" it so that it responds to a subsequent challenge with a boost of Torpedo AChR in a different manner.

We discovered evidence for mechanisms by which the therapy may work. Induction of immune responses can be blocked by passive transfer of antibody. For example, antibody to the D antigen is used clinically to prevent hemolytic disease of the fetus and newborn. Large amounts of antibody to the antigen bound to B lymphocytes can cross-link FcγRIIB receptors on B cells thereby triggering apoptosis.

This process is antigen-specific, but not epitope-specific, because the therapeutic antibodies are not directed at the same epitopes of the autoimmunogen involved in the pathological autoimmune response. This explains why antibodies to epitopes on the extracellular surface can be suppressed by cytoplasmic domain fragments. Induction of EAMG with human MIR/AChBP chimeras (which have no cytoplasmic or transmembrane domains) induced formation of antibodies to the cytoplasmic domains of muscle AChRs. Antibodies to the extracellular domain of AChRs cause focal lysis of the postsynaptic membrane and shedding of AChRs into the synaptic cleft. These shed muscle AChRs can both provoke the immune response to cytoplasmic domains and boost the response to extracellular domains. This feed-forward cycle of autoimmune stimulation to muscle AChRs could sustain EAMG and MG. This vicious cycle could also be the target of our therapy. Therapeutic vaccine protein, present in much greater amount than shed AChRs, produces high concentrations of antibodies to cytoplasmic domains, reversing the vicious cycle by driving apoptosis rather than stimulation of pathogenic B lymphocytes. We observed that administering weekly a mix of mAbs to the cytoplasmic domains of AChR subunits, but not normal rat IgG, partially suppressed development of the chronic phase of EAMG. This suggests that antibody-mediated feedback suppression contributes to the benefits of therapy.

Therapy rapidly reduced antibodies to the MIR, and after re-immunization with *Torpedo* AChR shifted predominant antibody isotypes from IgG2b (that fixes complement) to IgG1 (that does not). During therapy, suppression of antibody response to the MIR was not isotype-specific. After re-immunization with *Torpedo* AChR, resistance of treated rats to re-induction of EAMG was accompanied by a rapid increase of antibodies to the MIR. These data suggest that a distinct mechanism may be involved. Administering the therapeutic vaccine in IFA is more effective than in Titer-Max. IFA induces a predominantly Th2 biased response, while TiterMax induces a strong Th1 response. Shift of IgG subtypes towards the Th2-regulated IgG1 isotype by therapy, together with preference for a Th2-promoting adjuvant, suggests that therapy may involve a downregulation of Th1 responses specific to extracellular epitopes. Th1 cells induce synthesis of complement-fixing antibodies, which damage the postsynaptic membrane. Antigenic modulation is caused by crosslinking of AChRs by antibodies independent of complement. In MG patients, the predominant isotypes of anti-AChR antibodies are IgG1 and IgG3 (that fix complement). Complement-mediated destruction of AChRs may be more pathogenically significant than antigenic modulation. Autoantibodies from previously treated rats re-immunized with *Torpedo* AChR were ineffective at fixing complement, thus failed at causing or passively transferring EAMG, although they caused antigenic modulation. A similar observation was made when EAMG was induced by human MIR/AChBP chimera. Unlike *Torpedo* AChR, which primarily produced lgG2b antibodies to the MIR, the chimera generated very little IgG2b but high levels of lgGI antibodies to the MIR. Thus, although the chimera produced much higher antibody titers to the MIR chimera than did *Torpedo* AChR, EAMG induced by the chimera developed more slowly and was less severe than that induced by equivalent amounts of *Torpedo* AChR Autoantibodies to AChR are detected in 90% of MG patients and used as a diagnostic test for MG. There is not a close correlation between anti-AChR concentration and severity of MG. Besides variability in specificities of the antibodies to the AChR, another factor contributing to this lack of correlation may be differences in isotypes of the antibodies to AChR in various patients.

Suppression of ongoing EAMG by oral administration of bacterially-expressed human or rat AChR $\alpha 1$ extracellular domains was associated with downregulation of the Th1 response. Increase in Foxp3 expression in EAMG rats following the oral treatment suggested involvement of Foxp3+ regulatory T cells (Treg) in the antigen-specific immunesuppression. It has been reported that antigen-specific Treg suppress protective Th1 responses in infectious diseases. Administration of antigen to compartments rich in Treg results in specific suppression of the autoimmune response. Treg could also be activated by Treg epitopes in antibodies in response to binding antigen. Contributions of Treg to antigen-specific immunosuppression by treatment with cytoplasmic domains of AChRs remain to be determined.

Specific immunosuppressive therapy with human AChR cytoplasmic domains may be even more effective in MG patients than it is in rats with EAMG. Rats strongly avoid making autoantibodies. For example, rats immunized with human MIR/AChBP chimera develop EAMG, but even though only 4 of the 42 human muscle AChR $\alpha 1$ subunit amino acids in the chimera differ from rat $\alpha 1$ (10%), 82% of the antibodies to AChR are selective for human versus rat muscle AChR. Cytoplasmic domain sequences differ between humans and rats by 13%. Thus, specific immunosuppressive therapy of MG with human cytoplasmic domains might be >5 fold more potent than therapy of EAMG.

Translation of the therapy to human MG will require a substitute adjuvant for IFA. Aluminum salts (alum) are the most widely used adjuvants for human vaccines and will be evaluated in rats with EAMG. Alum induces a strong Th2 response with little or no Th1 response. It is likely that alum will be as effective as IFA considering the beneficial effects of Th2 response in the therapy.

The basic approach used here to suppress a pathological autoimmune response to the extracellular domain of vaccination with cytoplasmic domains of the autoimmunogen should be applicable to other antibody-mediated autoimmune responses to transmembrane proteins, for example autoimmune responses to glutamate receptors).

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the methods of the present invention do not rely on the particular order of steps set forth herein, the particular order of the steps should not be construed as limitation on the claims. Any claims directed to the methods of the present invention should not be limited to the performance of their steps in the order written, and one skilled in the art can readily appreciate that the steps may be varied and still remain within the spirit and scope of the present invention. Moreover, every document referenced herein, directly or indirectly, is incorporated in its entirety as if fully set forth herein.

We claim:

1. A vaccine composition for the treatment of myasthenia gravis, the vaccine composition comprising:
   one or more acetylcholine receptor subunit contiguous cytoplasmic domain constructs, the one or more acetylcholine receptor subunit contiguous cytoplasmic domain constructs comprising two or more of cytoplasmic domains of acetylcholine receptor subunits and immunogenic fragments of cytoplasmic domains of acetylcholine receptor subunits, wherein the cytoplasmic domains of acetylcholine receptor subunits and/or the one or more immunogenic fragments of cytoplasmic domains of acetylcholine receptor subunits are selected from the group consisting of: cytoplasmic domains and/or immunogenic fragments of cytoplasmic domains of AChR α1 subunit (SEQ ID NO 1), cytoplasmic domains and/or immunogenic fragments of cytoplasmic domains of AChR β1 subunit (SEQ ID NO 2), cytoplasmic domains and/or immunogenic fragments of cytoplasmic domains of AChR γ subunit (SEQ ID NO 3), cytoplasmic domains and/or immunogenic fragments of cytoplasmic domains of AChR δ subunit (SEQ ID NO 4), and cytoplasmic domains and/or immunogenic fragments of cytoplasmic domains of AChR ε subunit (SEQ ID NO 5); wherein immunogenic fragments are defined as biologically active polypeptide subsequences of peptides; and
   an adjuvant.

2. The vaccine composition according to claim 1, wherein the adjuvant comprises an aluminum salt.

3. The vaccine composition according to claim 2, wherein the aluminum salt is selected from the group consisting of aluminum hydroxide, aluminum phosphate, aluminum potassium sulfate, aluminum hydroxyphosphate sulfate.

4. The vaccine composition according to claim 1, wherein the adjuvant is selected from the group consisting of sorbitan trioleate emulsified in squalene oil and polysorbate 80 aluminum hydroxide adsorbent, and aluminum hydroxide adsorbant plus monophosphoryl lipid A.

5. The vaccine composition according to claim 1, wherein the adjuvant induces a Th2 response.

6. The vaccine composition according to claim 5, wherein the adjuvant induces a greater Th2 response than Th1 response.

7. The vaccine composition according to claim 1, wherein the one or more acetylcholine receptor subunit contiguous cytoplasmic domain constructs comprises a cytoplasmic domain construct consisting of a mixture of cytoplasmic domains and/or cytoplasmic domain immunogenic fragments of acetylcholine receptor subunits, the cytoplasmic domains and/or cytoplasmic domain immunogenic fragments of the acetylcholine receptor subunits consisting of cytoplasmic domains and/or cytoplasmic domain immunogenic fragments of the AChR β1 subunit (SEQ ID NO 2), cytoplasmic domains and/or cytoplasmic domain immunogenic fragments of the AChR α1 subunit (SEQ ID NO. 1), and cytoplasmic domains and/or cytoplasmic domain immunogenic fragments of the AChR γ subunit (SEQ ID NO 3).

8. The vaccine composition according to claim 1, wherein the one or more acetylcholine receptor subunit contiguous cytoplasmic domain constructs comprises a cytoplasmic domain construct consisting of a mixture of cytoplasmic domains and/or cytoplasmic domain immunogenic fragments of the acetylcholine receptor subunits consisting of cytoplasmic domains and/or cytoplasmic domain immunogenic fragments of the AChR ε subunit (SEQ ID NO 5), cytoplasmic domains and/or cytoplasmic domain immunogenic fragments of the AChR α1 subunit (SEQ ID NO 1), and cytoplasmic domains and/or cytoplasmic domain immunogenic fragments of the AChR δ subunit (SEQ ID NO 4).

9. A method of treating or preventing the onset of chronic myasthenia gravis in a patient, comprising:
    administering a vaccine composition, the vaccine composition comprising:
        one or more acetylcholine receptor subunit contiguous cytoplasmic domain constructs, the one or more acetylcholine receptor subunit contiguous cytoplasmic domain constructs comprising two or more of cytoplasmic domains of acetylcholine receptor subunits and immunogenic fragments of cytoplasmic domains of acetylcholine receptor subunits, wherein the cytoplasmic domains of acetylcholine receptor subunits and/or the one or more immunogenic fragments of cytoplasmic domains of acetylcholine receptor subunits are selected from the group consisting of: cytoplasmic domains and/or immunogenic fragments of cytoplasmic domains of AChR α1 subunit subunit (SEQ ID NO 1), cytoplasmic domains and/or immunogenic fragments of cytoplasmic domains of AChR β1 subunit (SEQ ID NO 2), cytoplasmic domains and/or immunogenic fragments of cytoplasmic domains of AChR γ subunit (SEQ ID NO 3), cytoplasmic domains and/or immunogenic fragments of cytoplasmic domains of AChR δ subunit (SEQ ID NO 4), and cytoplasmic domains and/or immunogenic fragments of cytoplasmic domains of AChR ε subunit (SEQ ID NO 5); wherein immunogenic fragments are defined as biologically active polypeptide subsequences of peptides; and
    an adjuvant.

10. A method of treating myasthenia gravis in a patient in need thereof, comprising:
    administering a vaccine composition, the vaccine composition comprising:
        one or more acetylcholine receptor subunit contiguous cytoplasmic domain constructs, the one or more acetylcholine receptor subunit contiguous cytoplasmic domain constructs comprising two or more of cytoplasmic domains of acetylcholine receptor subunits and immunogenic fragments of cytoplasmic domains of acetylcholine receptor subunits, wherein the cytoplasmic domains of acetylcholine receptor subunits and/or the one or more immunogenic fragments of cytoplasmic domains of acetylcholine receptor subunits are selected from the group consisting of: cytoplasmic domains and/or immunogenic fragments of cytoplasmic domains of AChR α1 subunit (SEQ ID NO 1), cytoplasmic domains and/or immunogenic fragments of cytoplasmic domains of AChR β1 subunit (SEQ ID NO 2), cytoplasmic domains and/or immunogenic fragments of cytoplasmic domains of AChR γ subunit (SEQ ID NO 3), cytoplasmic domains and/or immunogenic fragments of cytoplasmic domains of AChR δ subunit (SEQ ID NO 4), and cytoplasmic domains and/or immunogenic fragments of cytoplasmic domains of AChR ε subunit (SEQ ID NO 5); wherein immunogenic fragments are defined as biologically active polypeptide subsequences of peptides; and
    an adjuvant.

11. The method according to claim 10, wherein the patient has acute myasthenia gravis.

12. The method according to claim 10, wherein the patient has chronic myasthenia gravis.

13. The method according claim 10, wherein the vaccine composition is administered once a week.

14. The method according to claim 10, wherein the vaccine composition is administered once every two weeks.

15. The method according to claim 10, wherein the vaccine composition administered comprises 1 mg acetylcholine receptor subunit contiguous cytoplasmic domain construct.

16. The method according to claim 10, wherein the vaccine composition administered comprises 0.5 mg acetylcholine receptor subunit contiguous cytoplasmic domain construct.

* * * * *

SEQUENCE LISTING

<160> NUMBER OF SEQ ID NOS: 15

<210> SEQ ID NO 1
<211> LENGTH: 436
<212> TYPE: PRT
<213> ORGANISM: Homo sapiens

<400> SEQUENCE: 1

```
Ser Glu His Glu Thr Arg Leu Val Ala Lys Leu Phe Lys Asp Tyr Ser
1               5                   10                  15

Ser Val Val Arg Pro Val Glu Asp His Arg Gln Val Val Glu Val Thr
                20                  25                  30

Val Gly Leu Gln Leu Ile Gln Leu Ile Asn Val Asp Glu Val Asn Gln
            35                  40                  45

Ile Val Thr Thr Asn Val Arg Leu Lys Gln Gln Trp Val Asp Tyr Asn
        50                  55                  60

Leu Lys Trp Asn Pro Asp Asp Tyr Gly Gly Val Lys Lys Ile His Ile
65                  70                  75                  80

Pro Ser Glu Lys Ile Trp Arg Pro Asp Leu Val Leu Tyr Asn Asn Ala
                85                  90                  95

Asp Gly Asp Phe Ala Ile Val Lys Phe Thr Lys Val Leu Leu Gln Tyr
            100                 105                 110

Thr Gly His Ile Thr Trp Thr Pro Pro Ala Ile Phe Lys Ser Tyr Cys
        115                 120                 125

Glu Ile Ile Val Thr His Phe Pro Phe Asp Gln Gln Asn Cys Ser Met
    130                 135                 140

Lys Leu Gly Thr Trp Thr Tyr Asp Gly Ser Val Val Ala Ile Asn Pro
145                 150                 155                 160

Glu Ser Asp Gln Pro Asp Leu Ser Asn Phe Met Glu Ser Gly Glu Trp
                165                 170                 175

Val Ile Lys Glu Ser Arg Gly Trp Lys His Ser Val Thr Tyr Ser Cys
            180                 185                 190

Cys Pro Asp Thr Pro Tyr Leu Asp Ile Thr Tyr His Phe Val Met Gln
        195                 200                 205

Arg Leu Pro Leu Tyr Phe Ile Val Asn Ile Ile Pro Cys Leu Leu Phe
    210                 215                 220

Ser Phe Leu Thr Gly Leu Val Phe Tyr Leu Pro Thr Asp Ser Gly Glu
225                 230                 235                 240

Lys Met Thr Leu Ser Ile Ser Val Leu Leu Ser Leu Thr Val Phe Leu
                245                 250                 255

Leu Val Ile Val Glu Leu Ile Pro Ser Thr Ser Ser Ala Val Pro Leu
            260                 265                 270

Ile Gly Lys Tyr Met Leu Phe Thr Met Val Phe Val Ile Ala Ser Ile
        275                 280                 285

Ile Ile Thr Val Ile Val Ile Asn Thr His His Arg Ser Pro Ser Thr
    290                 295                 300

His Val Met Pro Asn Trp Val Arg Lys Val Phe Ile Asp Thr Ile Pro
305                 310                 315                 320

Asn Ile Met Phe Phe Ser Thr Met Lys Arg Pro Ser Arg Glu Lys Gln
                325                 330                 335

Asp Lys Lys Ile Phe Thr Glu Asp Ile Asp Ile Ser Asp Ile Ser Gly
            340                 345                 350

Lys Pro Gly Pro Pro Pro Met Gly Phe His Ser Pro Leu Ile Lys His
        355                 360                 365
```

```
Pro Glu Val Lys Ser Ala Ile Glu Gly Ile Lys Tyr Ile Ala Glu Thr
    370                 375                 380

Met Lys Ser Asp Gln Glu Ser Asn Asn Ala Ala Ala Glu Trp Lys Tyr
385                 390                 395                 400

Val Ala Met Val Met Asp His Ile Leu Leu Gly Val Phe Met Leu Val
                405                 410                 415

Cys Ile Ile Gly Thr Leu Ala Val Phe Ala Gly Arg Leu Ile Glu Leu
                420                 425                 430

Asn Gln Gln Gly
            435

<210> SEQ ID NO 2
<211> LENGTH: 478
<212> TYPE: PRT
<213> ORGANISM: Homo sapiens

<400> SEQUENCE: 2

Ser Glu Ala Glu Gly Arg Leu Arg Glu Lys Leu Phe Ser Gly Tyr Asp
1               5                   10                  15

Ser Ser Val Arg Pro Ala Arg Glu Val Gly Asp Arg Val Arg Val Ser
                20                  25                  30

Val Gly Leu Ile Leu Ala Gln Leu Ile Ser Leu Asn Glu Lys Asp Glu
            35                  40                  45

Glu Met Ser Thr Lys Val Tyr Leu Asp Leu Glu Trp Thr Asp Tyr Arg
50                  55                  60

Leu Ser Trp Asp Pro Ala Glu His Asp Gly Ile Asp Ser Leu Arg Ile
65                  70                  75                  80

Thr Ala Glu Ser Val Trp Leu Pro Asp Val Val Leu Leu Asn Asn Asn
                85                  90                  95

Asp Gly Asn Phe Asp Val Ala Leu Asp Ile Ser Val Val Ser Ser
                100                 105                 110

Asp Gly Ser Val Arg Trp Gln Pro Pro Gly Ile Tyr Arg Ser Ser Cys
            115                 120                 125

Ser Ile Gln Val Thr Tyr Phe Pro Phe Asp Trp Gln Asn Cys Thr Met
    130                 135                 140

Val Phe Ser Ser Tyr Ser Tyr Asp Ser Ser Glu Val Ser Leu Gln Thr
145                 150                 155                 160

Gly Leu Gly Pro Asp Gly Gln Gly His Gln Glu Ile His Ile His Glu
                165                 170                 175

Gly Thr Phe Ile Glu Asn Gly Gln Trp Glu Ile Ile His Lys Pro Ser
            180                 185                 190

Arg Leu Ile Gln Pro Pro Gly Asp Pro Arg Gly Gly Arg Glu Gly Gln
        195                 200                 205

Arg Gln Glu Val Ile Phe Tyr Leu Ile Ile Arg Arg Lys Pro Leu Phe
    210                 215                 220

Tyr Leu Val Asn Val Ile Ala Pro Cys Ile Leu Ile Thr Leu Leu Ala
225                 230                 235                 240

Ile Phe Val Phe Tyr Leu Pro Pro Asp Ala Gly Glu Lys Met Gly Leu
                245                 250                 255

Ser Ile Phe Ala Leu Leu Thr Leu Thr Val Phe Leu Leu Leu Leu Ala
            260                 265                 270

Asp Lys Val Pro Glu Thr Ser Leu Ser Val Pro Ile Ile Ile Lys Tyr
        275                 280                 285

Leu Met Phe Thr Met Val Leu Val Thr Phe Ser Val Ile Leu Ser Val
    290                 295                 300
```

-continued

```
Val Val Leu Asn Leu His His Arg Ser Pro His Thr His Gln Met Pro
305                 310                 315                 320

Leu Trp Val Arg Gln Ile Phe Ile His Lys Leu Pro Leu Tyr Leu Arg
                325                 330                 335

Leu Lys Arg Pro Lys Pro Glu Arg Asp Leu Met Pro Glu Pro Pro His
            340                 345                 350

Cys Ser Ser Pro Gly Ser Gly Trp Gly Arg Gly Thr Asp Glu Tyr Phe
        355                 360                 365

Ile Arg Lys Pro Pro Ser Asp Phe Leu Phe Pro Lys Pro Asn Arg Phe
    370                 375                 380

Gln Pro Glu Leu Ser Ala Pro Asp Leu Arg Arg Phe Ile Asp Gly Pro
385                 390                 395                 400

Asn Arg Ala Val Ala Leu Leu Pro Glu Leu Arg Glu Val Val Ser Ser
                405                 410                 415

Ile Ser Tyr Ile Ala Arg Gln Leu Gln Glu Gln Glu Asp His Asp Ala
            420                 425                 430

Leu Lys Glu Asp Trp Gln Phe Val Ala Met Val Val Asp Arg Leu Phe
        435                 440                 445

Leu Trp Thr Phe Ile Ile Phe Thr Ser Val Gly Thr Leu Val Ile Phe
    450                 455                 460

Leu Asp Ala Thr Tyr His Leu Pro Pro Asp Pro Phe Pro
465                 470                 475

<210> SEQ ID NO 3
<211> LENGTH: 495
<212> TYPE: PRT
<213> ORGANISM: Homo sapiens

<400> SEQUENCE: 3

Arg Asn Gln Glu Glu Arg Leu Leu Ala Asp Leu Met Gln Asn Tyr Asp
1               5                   10                  15

Pro Asn Leu Arg Pro Ala Glu Arg Asp Ser Asp Val Val Asn Val Ser
                20                  25                  30

Leu Lys Leu Thr Leu Thr Asn Leu Ile Ser Leu Asn Glu Arg Glu Glu
            35                  40                  45

Ala Leu Thr Thr Asn Val Trp Ile Glu Met Gln Trp Cys Asp Tyr Arg
        50                  55                  60

Leu Arg Trp Asp Pro Arg Asp Tyr Glu Gly Leu Trp Val Leu Arg Val
65                  70                  75                  80

Pro Ser Thr Met Val Trp Arg Pro Asp Ile Val Leu Glu Asn Asn Val
                85                  90                  95

Asp Gly Val Phe Glu Val Ala Leu Tyr Cys Asn Val Leu Val Ser Pro
            100                 105                 110

Asp Gly Cys Ile Tyr Trp Leu Pro Pro Ala Ile Phe Arg Ser Ala Cys
        115                 120                 125

Ser Ile Ser Val Thr Tyr Phe Pro Phe Asp Trp Gln Asn Cys Ser Leu
    130                 135                 140

Ile Phe Gln Ser Gln Thr Tyr Ser Thr Asn Glu Ile Asp Leu Gln Leu
145                 150                 155                 160

Ser Gln Glu Asp Gly Gln Thr Ile Glu Trp Ile Phe Ile Asp Pro Glu
                165                 170                 175

Ala Phe Thr Glu Asn Gly Glu Trp Ala Ile Gln His Arg Pro Ala Lys
            180                 185                 190

Met Leu Leu Asp Pro Ala Ala Pro Ala Gln Glu Ala Gly His Gln Lys
```

```
            195                 200                 205
Val Val Phe Tyr Leu Leu Ile Gln Arg Lys Pro Leu Phe Tyr Val Ile
210                 215                 220

Asn Ile Ile Ala Pro Cys Val Leu Ile Ser Ser Val Ala Ile Leu Ile
225                 230                 235                 240

His Phe Leu Pro Ala Lys Ala Gly Gly Gln Lys Cys Thr Val Ala Ile
            245                 250                 255

Asn Val Leu Leu Ala Gln Thr Val Phe Leu Phe Leu Val Ala Lys Lys
            260                 265                 270

Val Pro Glu Thr Ser Gln Ala Val Pro Leu Ile Ser Lys Tyr Leu Thr
            275                 280                 285

Phe Leu Leu Val Val Thr Ile Leu Ile Val Val Asn Ala Val Val Val
290                 295                 300

Leu Asn Val Ser Leu Arg Ser Pro His Thr His Ser Met Ala Arg Gly
305                 310                 315                 320

Val Arg Lys Val Phe Leu Arg Leu Leu Pro Gln Leu Leu Arg Met His
            325                 330                 335

Val Arg Pro Leu Ala Pro Ala Val Gln Asp Thr Gln Ser Arg Leu
            340                 345                 350

Gln Asn Gly Ser Ser Gly Trp Ser Ile Thr Thr Gly Glu Glu Val Ala
            355                 360                 365

Leu Cys Leu Pro Arg Ser Glu Leu Leu Phe Gln Gln Trp Gln Arg Gln
370                 375                 380

Gly Leu Val Ala Ala Leu Glu Lys Leu Glu Lys Gly Pro Glu Leu
385                 390                 395                 400

Gly Leu Ser Gln Phe Cys Gly Ser Leu Lys Gln Ala Ala Pro Ala Ile
            405                 410                 415

Gln Ala Cys Val Glu Ala Cys Asn Leu Ile Ala Cys Ala Arg His Gln
            420                 425                 430

Gln Ser His Phe Asp Asn Gly Asn Glu Glu Trp Phe Leu Val Gly Arg
            435                 440                 445

Val Leu Asp Arg Val Cys Phe Leu Ala Met Leu Ser Leu Phe Ile Cys
450                 455                 460

Gly Thr Ala Gly Ile Phe Leu Met Ala His Tyr Asn Arg Val Pro Ala
465                 470                 475                 480

Leu Pro Phe Pro Gly Asp Pro Arg Pro Tyr Leu Pro Ser Pro Asp
            485                 490                 495

<210> SEQ ID NO 4
<211> LENGTH: 496
<212> TYPE: PRT
<213> ORGANISM: Homo sapiens

<400> SEQUENCE: 4

Leu Asn Glu Glu Glu Arg Leu Ile Arg His Leu Phe Gln Glu Lys Gly
1               5                   10                  15

Tyr Asn Lys Glu Leu Arg Pro Val Ala His Lys Glu Glu Ser Val Asp
            20                  25                  30

Val Ala Leu Ala Leu Thr Leu Ser Asn Leu Ile Ser Leu Lys Glu Val
        35                  40                  45

Glu Glu Thr Leu Thr Thr Asn Val Trp Ile Glu His Gly Trp Thr Asp
    50                  55                  60

Asn Arg Leu Lys Trp Asn Ala Glu Glu Phe Gly Asn Ile Ser Val Leu
65                  70                  75                  80
```

```
Arg Leu Pro Pro Asp Met Val Trp Leu Pro Glu Ile Val Leu Glu Asn
             85                  90                  95
Asn Asn Asp Gly Ser Phe Gln Ile Ser Tyr Ser Cys Asn Val Leu Val
        100                 105                 110
Tyr His Tyr Gly Phe Val Tyr Trp Leu Pro Pro Ala Ile Phe Arg Ser
    115                 120                 125
Ser Cys Pro Ile Ser Val Thr Tyr Phe Pro Phe Asp Trp Gln Asn Cys
130                 135                 140
Ser Leu Lys Phe Ser Ser Leu Lys Tyr Thr Ala Lys Glu Ile Thr Leu
145                 150                 155                 160
Ser Leu Lys Gln Asp Ala Lys Glu Asn Arg Thr Tyr Pro Val Glu Trp
                165                 170                 175
Ile Ile Ile Asp Pro Glu Gly Phe Thr Glu Asn Gly Glu Trp Glu Ile
            180                 185                 190
Val His Arg Pro Ala Arg Val Asn Val Asp Pro Arg Ala Pro Leu Asp
        195                 200                 205
Ser Pro Ser Arg Gln Asp Ile Thr Phe Tyr Leu Ile Ile Arg Arg Lys
    210                 215                 220
Pro Leu Phe Tyr Ile Ile Asn Ile Leu Val Pro Cys Val Leu Ile Ser
225                 230                 235                 240
Phe Met Val Asn Leu Val Phe Tyr Leu Pro Ala Asp Ser Gly Glu Lys
                245                 250                 255
Thr Ser Val Ala Ile Ser Val Leu Leu Ala Gln Ser Val Phe Leu Leu
            260                 265                 270
Leu Ile Ser Lys Arg Leu Pro Ala Thr Ser Met Ala Ile Pro Leu Ile
        275                 280                 285
Gly Lys Phe Leu Leu Phe Gly Met Val Leu Val Thr Met Val Val Val
    290                 295                 300
Ile Cys Val Ile Val Leu Asn Ile His Phe Arg Thr Pro Ser Thr His
305                 310                 315                 320
Val Leu Ser Glu Gly Val Lys Lys Leu Phe Leu Glu Thr Leu Pro Glu
                325                 330                 335
Leu Leu His Met Ser Arg Pro Ala Glu Asp Gly Pro Ser Pro Gly Ala
            340                 345                 350
Leu Val Arg Arg Ser Ser Ser Leu Gly Tyr Ile Ser Lys Ala Glu Glu
        355                 360                 365
Tyr Phe Leu Leu Lys Ser Arg Ser Asp Leu Met Phe Glu Lys Gln Ser
    370                 375                 380
Glu Arg His Gly Leu Ala Arg Arg Leu Thr Thr Ala Arg Arg Pro Pro
385                 390                 395                 400
Ala Ser Ser Glu Gln Ala Gln Gln Glu Leu Phe Asn Glu Leu Lys Pro
                405                 410                 415
Ala Val Asp Gly Ala Asn Phe Ile Val Asn His Met Arg Asp Gln Asn
            420                 425                 430
Asn Tyr Asn Glu Glu Lys Asp Ser Trp Asn Arg Val Ala Arg Thr Val
        435                 440                 445
Asp Arg Leu Cys Leu Phe Val Val Thr Pro Val Met Val Val Gly Thr
    450                 455                 460
Ala Trp Ile Phe Leu Gln Gly Val Tyr Asn Gln Pro Pro Pro Gln Pro
465                 470                 475                 480
Phe Pro Gly Asp Pro Tyr Ser Tyr Asn Val Gln Asp Lys Arg Phe Ile
                485                 490                 495
```

```
<210> SEQ ID NO 5
<211> LENGTH: 473
<212> TYPE: PRT
<213> ORGANISM: Homo sapiens

<400> SEQUENCE: 5

Lys Asn Glu Glu Leu Arg Leu Tyr His His Leu Phe Asn Asn Tyr Asp
1               5                   10                  15

Pro Gly Ser Arg Pro Val Arg Glu Pro Glu Asp Thr Val Thr Ile Ser
            20                  25                  30

Leu Lys Val Thr Leu Thr Asn Leu Ile Ser Leu Asn Glu Lys Glu Glu
        35                  40                  45

Thr Leu Thr Thr Ser Val Trp Ile Gly Ile Asp Trp Gln Asp Tyr Arg
    50                  55                  60

Leu Asn Tyr Ser Lys Asp Asp Phe Gly Gly Ile Glu Thr Leu Arg Val
65                  70                  75                  80

Pro Ser Glu Leu Val Trp Leu Pro Glu Ile Val Leu Glu Asn Asn Ile
                85                  90                  95

Asp Gly Gln Phe Gly Val Ala Tyr Asp Ala Asn Val Leu Val Tyr Glu
            100                 105                 110

Gly Gly Ser Val Thr Trp Leu Pro Pro Ala Ile Tyr Arg Ser Val Cys
        115                 120                 125

Ala Val Glu Val Thr Tyr Phe Pro Phe Asp Trp Gln Asn Cys Ser Leu
    130                 135                 140

Ile Phe Arg Ser Gln Thr Tyr Asn Ala Glu Glu Val Glu Phe Thr Phe
145                 150                 155                 160

Ala Val Asp Asn Asp Gly Lys Thr Ile Asn Lys Ile Asp Ile Asp Thr
                165                 170                 175

Glu Ala Tyr Thr Glu Asn Gly Glu Trp Ala Ile Asp Phe Cys Pro Gly
            180                 185                 190

Val Ile Arg Arg His His Gly Gly Ala Thr Asp Gly Pro Gly Glu Thr
        195                 200                 205

Asp Val Ile Tyr Ser Leu Ile Ile Arg Arg Lys Pro Leu Phe Tyr Val
    210                 215                 220

Ile Asn Ile Ile Val Pro Cys Val Leu Ile Ser Gly Leu Val Leu Leu
225                 230                 235                 240

Ala Tyr Phe Leu Pro Ala Gln Ala Gly Gly Gln Lys Cys Thr Val Ser
                245                 250                 255

Ile Asn Val Leu Leu Ala Gln Thr Val Phe Leu Phe Leu Ile Ala Gln
            260                 265                 270

Lys Ile Pro Glu Thr Ser Leu Ser Val Pro Leu Leu Gly Arg Phe Leu
        275                 280                 285

Ile Phe Val Met Val Val Ala Thr Leu Ile Val Met Asn Cys Val Ile
    290                 295                 300

Val Leu Asn Val Ser Gln Arg Thr Pro Thr Thr His Ala Met Ser Pro
305                 310                 315                 320

Arg Leu Arg His Val Leu Leu Glu Leu Leu Pro Arg Leu Leu Gly Ser
                325                 330                 335

Pro Pro Pro Pro Glu Ala Pro Arg Ala Ala Ser Pro Pro Arg Arg Ala
            340                 345                 350

Ser Ser Val Gly Leu Leu Leu Arg Ala Glu Glu Leu Ile Leu Lys Lys
        355                 360                 365

Pro Arg Ser Glu Leu Val Phe Glu Gly Gln Arg His Arg Gln Gly Thr
    370                 375                 380
```

```
Trp Thr Ala Ala Phe Cys Gln Ser Leu Gly Ala Ala Pro Glu Val
385                 390                 395                 400

Arg Cys Cys Val Asp Ala Val Asn Phe Val Ala Glu Ser Thr Arg Asp
            405                 410                 415

Gln Glu Ala Thr Gly Glu Glu Val Ser Asp Trp Val Arg Met Gly Asn
            420                 425                 430

Ala Leu Asp Asn Ile Cys Phe Trp Ala Ala Leu Val Leu Phe Ser Val
            435                 440                 445

Gly Ser Ser Leu Ile Phe Leu Gly Ala Tyr Phe Asn Arg Val Pro Asp
        450                 455                 460

Leu Pro Tyr Ala Pro Cys Ile Gln Pro
465                 470
```

```
<210> SEQ ID NO 6
<211> LENGTH: 35
<212> TYPE: DNA
<213> ORGANISM: Artificial Sequence
<220> FEATURE:
<223> OTHER INFORMATION: Synthetic (primer alpha 1)

<400> SEQUENCE: 6
ttcatcacta gtaacacaca ccaccgctca cccag                          35

<210> SEQ ID NO 7
<211> LENGTH: 36
<212> TYPE: DNA
<213> ORGANISM: Artificial Sequence
<220> FEATURE:
<223> OTHER INFORMATION: Synthetic (primer alpha 1)

<400> SEQUENCE: 7
aagagggatc cgtggtccat caccattgca acgtac                         36

<210> SEQ ID NO 8
<211> LENGTH: 33
<212> TYPE: DNA
<213> ORGANISM: Artificial Sequence
<220> FEATURE:
<223> OTHER INFORMATION: Synthetic (primer beta 1)

<400> SEQUENCE: 8
aattctacat atgcaccacc gctcacccca cac                            33

<210> SEQ ID NO 9
<211> LENGTH: 37
<212> TYPE: DNA
<213> ORGANISM: Artificial Sequence
<220> FEATURE:
<223> OTHER INFORMATION: Synthetic (primer beta 1)

<400> SEQUENCE: 9
acacagacta gtgcggtcca ctaccatggc cacaaac                        37

<210> SEQ ID NO 10
<211> LENGTH: 32
<212> TYPE: DNA
<213> ORGANISM: Artificial Sequence
<220> FEATURE:
<223> OTHER INFORMATION: Synthetic (primer gamma)

<400> SEQUENCE: 10
tcaatggatc cttgcggtct ccacacacac ac                             32
```

```
<210> SEQ ID NO 11
<211> LENGTH: 36
<212> TYPE: DNA
<213> ORGANISM: Artificial Sequence
<220> FEATURE:
<223> OTHER INFORMATION: Synthetic (primer gamma)

<400> SEQUENCE: 11
atgaactcga ggcggtccag cactcggccc accagg                                 36

<210> SEQ ID NO 12
<211> LENGTH: 39
<212> TYPE: DNA
<213> ORGANISM: Artificial Sequence
<220> FEATURE:
<223> OTHER INFORMATION: Synthetic (primer delta)

<400> SEQUENCE: 12
tgataggatc ccacttccga acacccagca cccatgtgc                              39

<210> SEQ ID NO 13
<211> LENGTH: 33
<212> TYPE: DNA
<213> ORGANISM: Artificial Sequence
<220> FEATURE:
<223> OTHER INFORMATION: Synthetic (primer delta)

<400> SEQUENCE: 13
aatatctcga ggcggtccac tgtgcgggcc act                                    33

<210> SEQ ID NO 14
<211> LENGTH: 32
<212> TYPE: DNA
<213> ORGANISM: Artificial Sequence
<220> FEATURE:
<223> OTHER INFORMATION: Synthetic (primer epsilon)

<400> SEQUENCE: 14
atactccata tgtcccagcg gacgcccacc ac                                     32

<210> SEQ ID NO 15
<211> LENGTH: 33
<212> TYPE: DNA
<213> ORGANISM: Artificial Sequence
<220> FEATURE:
<223> OTHER INFORMATION: Synthetic (primer epsilon)

<400> SEQUENCE: 15
aatatctcga ggcggtccac tgtgcgggcc act                                    33
```